US008791254B2

(12) United States Patent
Vitcak et al.

(10) Patent No.: US 8,791,254 B2
(45) Date of Patent: Jul. 29, 2014

(54) CYCLIC HYDROFLUOROETHER COMPOUNDS AND PROCESSES FOR THEIR PREPARATION AND USE

(75) Inventors: Daniel R. Vitcak, Cottage Grove, MN (US); Richard M. Flynn, Mahtomedi, MN (US); Michael G. Costello, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1463 days.

(21) Appl. No.: 11/567,602

(22) Filed: Dec. 6, 2006

(65) Prior Publication Data
US 2007/0267464 A1 Nov. 22, 2007

Related U.S. Application Data

(60) Provisional application No. 60/747,742, filed on May 19, 2006.

(51) Int. Cl.
C07D 309/10 (2006.01)

(52) U.S. Cl.
USPC ............ 544/78; 544/174; 549/378; 549/415; 549/416; 549/472; 549/475

(58) Field of Classification Search
USPC ............ 544/78, 174; 549/378, 415, 416, 472, 549/475
See application file for complete search history.

(56) References Cited

U.S. PATENT DOCUMENTS

| 2,713,593 | A | | 7/1955 | Brice et al. | |
|---|---|---|---|---|---|
| 3,342,777 | A | | 9/1967 | Howard | |
| 3,700,695 | A | * | 10/1972 | Carr et al. | 549/420 |
| 3,903,012 | A | | 9/1975 | Brandreth | |
| 4,024,192 | A | | 5/1977 | Benninger et al. | |
| 4,058,578 | A | * | 11/1977 | Kuhls et al. | 525/276 |
| 4,067,884 | A | * | 1/1978 | Martini | 549/378 |
| 4,118,399 | A | * | 10/1978 | Martini | 549/274 |
| 4,136,121 | A | | 1/1979 | Martini et al. | |
| 4,143,078 | A | | 3/1979 | Gibbs et al. | |
| 4,169,807 | A | | 10/1979 | Zuber | |
| 4,172,851 | A | | 10/1979 | Childs | |
| 4,275,225 | A | | 6/1981 | Krespan | |
| 4,576,752 | A | | 3/1986 | Krespan | |
| 4,736,045 | A | * | 4/1988 | Drakesmith et al. | 549/380 |
| 5,104,034 | A | | 4/1992 | Hansen et al. | |
| 5,125,978 | A | | 6/1992 | Flynn et al. | |
| 5,182,342 | A | | 1/1993 | Feiring et al. | |
| 5,210,106 | A | | 5/1993 | Dams et al. | |
| 5,539,008 | A | | 7/1996 | Dams et al. | |
| 5,696,308 | A | | 12/1997 | Burgess et al. | |
| 5,750,797 | A | | 5/1998 | Vitcak et al. | |
| 5,925,611 | A | | 7/1999 | Flynn et al. | |
| 6,013,795 | A | | 1/2000 | Manzara et al. | |
| 6,023,002 | A | | 2/2000 | Behr et al. | |
| 6,046,368 | A | | 4/2000 | Lamanna et al. | |
| 6,080,448 | A | | 6/2000 | Leiner et al. | |
| RE37,119 | E | | 4/2001 | Sherwood | |
| 6,303,080 | B1 | | 10/2001 | Tuma | |
| 6,313,359 | B1 | | 11/2001 | Tung et al. | |
| 6,361,713 | B1 | | 3/2002 | Moore et al. | |
| 6,362,379 | B2 | | 3/2002 | Moore et al. | |
| 6,374,907 | B1 | | 4/2002 | Tousignant et al. | |
| 6,394,107 | B1 | | 5/2002 | Kesari et al. | |
| 6,399,729 | B1 | | 6/2002 | Farnham et al. | |
| 6,407,282 | B1 | | 6/2002 | Murata et al. | |
| 6,573,235 | B1 | | 6/2003 | Surbled et al. | |
| 6,759,374 | B2 | | 7/2004 | Milbrath et al. | |
| 6,953,082 | B2 | | 10/2005 | Costello et al. | |
| 7,385,089 | B2 | | 6/2008 | Costello et al. | |
| 2002/0094944 | A1 | * | 7/2002 | Flynn et al. | 510/412 |
| 2003/0019841 | A1 | | 1/2003 | Kesari et al. | |
| 2003/0027732 | A1 | | 2/2003 | Howell et al. | |
| 2003/0089877 | A1 | | 5/2003 | Rivers et al. | |
| 2004/0192974 | A1 | | 9/2004 | Navarrini et al. | |
| 2004/0267053 | A1 | | 12/2004 | Okazoe et al. | |
| 2005/0224747 | A1 | | 10/2005 | Costello et al. | |
| 2006/0068283 | A1 | | 3/2006 | Segawa et al. | |
| 2006/0128821 | A1 | | 6/2006 | Owens et al. | |
| 2006/0205172 | A1 | | 9/2006 | Gerlach et al. | |
| 2007/0015865 | A1 | | 1/2007 | Hintzer et al. | |
| 2007/0051916 | A1 | | 3/2007 | Flynn et al. | |
| 2007/0072985 | A1 | | 3/2007 | Hintzer et al. | |

(Continued)

FOREIGN PATENT DOCUMENTS

| DE | 1294949 | 5/1969 |
|---|---|---|
| EP | 0 404 076 | 12/1990 |
| EP | 0 496 415 | 7/1992 |
| FR | 2 287 432 | 10/1974 |
| JP | 2006/290779 | 10/2006 |
| WO | WO 84/02909 | 8/1984 |

OTHER PUBLICATIONS

Abe et. al. Journal of Fluorine Chemistry 1980, 15(5), 353-80.*
Costello, M. J.; Flynn, R. M; Owens, J. G. Kirk-Othmer Encyclopedia of Chemical Technology, 5th ed.; Seidel, A., Ed.; John Wiley & Sons, Inc.: Hoboken, NJ, 2004; vol. 11, pp. 877-888.*
Middleton, W J et al., "Hydrogen Bonding in FluoroAlcohols", Journal of the American Chemical Society, vol. 86, No. 22, 1964, pp. 4948-4952, XP002456853.
Database Beilstein, Beilstein Institute for Organic Chemistry, Frankfurt-Main, DE; XP002456854, Database accession No. BRN: 6084978 abstract & US 4576752, Mar. 18, 1986.
Database Beilstein, Beilstein Institute for Organic Chemistry, Frankfurt-Main, DE; XP002456855, Database accession No. BRN: 3400232 abstract & US 6407282, Jun. 18, 2002.

(Continued)

Primary Examiner — David K O Dell

(57) ABSTRACT

A hydrofluoroether compound comprises at least one five- or six-membered, perfluorinated heterocyclic ring, each ring comprising four or five ring carbon atoms and one or two catenated heteroatoms selected from divalent ether oxygen atoms and trivalent nitrogen atoms, at least one of the catenated heteroatoms being a divalent ether oxygen atom, and each of the ring carbon atoms adjacent to the divalent ether oxygen atom bearing a fluorochemical group that comprises a tetrafluoroethylidene moiety (—$(CF_3)CF$—) that is directly bonded to the ring carbon atom, the fluorochemical group optionally comprising at least one catenated heteroatom selected from divalent ether oxygen atoms and trivalent nitrogen atoms.

15 Claims, No Drawings

(56) References Cited

U.S. PATENT DOCUMENTS

2007/0163710 A1 7/2007 Costello et al.
2008/0139683 A1 6/2008 Flynn et al.
2008/0269512 A1 10/2008 Lovis et al.

OTHER PUBLICATIONS

Database Beilstein, Beilstein Institute for Organic Chemistry, Frankfurt-Main, DE; XP002456856, Database accession No. BRN:30805 abstract & US 6362379, Mar. 26, 2002.
Database Beilstein, Beilstein Institute for Organic Chemistry, Frankfurt-Main, DE; XP002456857, Database accession No. BRN:6041338 abstract & J. Appl. Chem. USSR, vol. 56, No. 4, 1983, pp. 902-903.
R.E. Banks in *Preparation, Properties, and Industrial applications of Organofluorine Compounds*, pp. 19-43, Halsted Press, New York (1982).
Research Disclosures, No. 40576, p. 81 (Jan. 1998).
Barker et al., "2,3,5-Tri-*O*-benzyl-D-ribosyl and -L-arabinosyl Bromides", *Journal of Organic Chemistry*, vol. 26, (1961), pp. 4605-4609.
Nandi et al., "Synthesis of chiral *trans*-fused pyrano[3,2-*c*][2]benzoxocines from D-mannose by regioselective 8-*endo*-aryl radical cyclization", *Tetrahedron Letters*, 43, (2002), pp. 5977-5980.

\* cited by examiner

CYCLIC HYDROFLUOROETHER COMPOUNDS AND PROCESSES FOR THEIR PREPARATION AND USE

STATEMENT OF PRIORITY

This application claims the priority of U.S. Provisional Application No. 60/747,742 filed May 19, 2006, the contents of which are hereby incorporated by reference.

FIELD

This invention relates to partially-fluorinated ether compounds. In other aspects, this invention also relates to processes for preparing partially-fluorinated ether compounds and to processes for their use.

BACKGROUND

Hydrofluoroether compounds (HFEs) comprise a class of commercially valuable chemical compounds. In a number of applications, hydrofluoroethers have been found to be useful as replacements for chlorofluorocarbons (CFCs), which are currently disfavored and regulated due to the adverse effects that CFCs are believed to have on the environment. Unlike CFCs, hydrofluoroether compounds that contain fluorine as the only halogen have essentially no effect on the earth's ozone layer. Such hydrofluoroether compounds are thus said to exhibit an "ozone depletion potential" of zero. In addition, such HFEs are typically more easily degraded within the earth's atmosphere, which results in a low global warming potential.

Hydrofluoroether compounds have been prepared by various different methods including, for example, alkylation of perfluorinated acid fluorides (prepared by electrochemical fluorination or by direct fluorination), alkylation of perfluorinated ketones (prepared by reaction of perfluorinated acid fluorides and perfluorinated olefins), and photooxidation of tetrafluoroethylene (TFE) followed by reductive stabilization. Such methods have various advantages and disadvantages. For example, the latter method requires the handling of a relatively hazardous reagent, TFE, and also provides a broad product mixture that generally requires extensive purification. Such methods also have generally not been suitable for the direct formation of cyclic HFEs (that is, for the formation of a ring structure during an alkylation step).

SUMMARY

In view of an increasing demand for environmentally friendly chemical compounds (preferably, compounds having an ozone depletion potential of zero and/or a low global warming potential), we recognize that there exists an ongoing need for HFEs that can meet the performance requirements of a variety of different applications (for example, boiling points of 150° C. or higher), as well as for efficient and cost-effective processes for their preparation. Such processes will preferably be capable of flexibly and controllably producing hydrofluoroether compounds having tailored structures and physical properties, without producing a broad product mixture.

Briefly, in one aspect, this invention provides a hydrofluoroether compound comprising at least one (preferably, one or two) five- or six-membered, perfluorinated heterocyclic ring(s), each ring comprising four or five ring carbon atoms and one or two catenated (that is, in-chain) heteroatoms selected from divalent ether oxygen atoms and trivalent nitrogen atoms, at least one of the catenated heteroatoms being a divalent ether oxygen atom, and each of the ring carbon atoms adjacent to the divalent ether oxygen atom bearing a fluorochemical group that comprises a tetrafluoroethylidene moiety ($-(CF_3)CF-$) that is directly bonded to the ring carbon atom, the fluorochemical group optionally comprising at least one catenated heteroatom selected from divalent ether oxygen atoms and trivalent nitrogen atoms.

Preferably, one of the ring carbon atoms that bears a fluorochemical group further bears a fluorine atom, and the other further bears an alkoxy or fluoroalkoxy group or, when at least a second ring is present, a divalent oxyalkyleneoxy or oxyfluoroalkyleneoxy group that is bonded to a ring carbon atom of the second (or higher) ring. More preferably, the remaining ring carbon atoms (that is, those that are not adjacent to the divalent ether oxygen atom) can be independently unsubstituted (bearing only fluorine) or perfluoroalkyl-monosubstituted (bearing a fluorine atom and a perfluoroalkyl group that optionally contains at least one catenated heteroatom).

The rings of the hydrofluoroether compound are preferably identical. Preferably, each ring comprises only one catenated heteroatom, and/or each fluorochemical group is a branched perfluoroalkyl group that optionally comprises at least one catenated heteroatom selected from divalent ether oxygen atoms and trivalent nitrogen atoms (preferably, divalent ether oxygen atoms).

It has been discovered that a versatile new class of hydrofluoroether compounds can be produced in good yield by a simple process comprising the alkylation of fluorochemical alkoxides prepared by the reaction of certain fluorochemical diketones (those having branched fluoroalkyl or perfluoroalkyl terminal groups that optionally comprise at least one catenated heteroatom selected from divalent ether oxygen atoms and trivalent nitrogen atoms) with an anhydrous alkali metal fluoride (for example, potassium fluoride or cesium fluoride) or anhydrous silver fluoride (preferably, in an anhydrous polar, aprotic solvent). Surprisingly, a cyclization reaction occurs during the alkylation step, in spite of the presence of the bulky, branched terminal groups. By varying the structure of the starting diketones, cyclic HFEs having tailored structures and physical properties can be controllably obtained.

The HFEs of the invention can be used in a number of different applications including, for example, use as a solvent in coating deposition, as a cleaning or drying fluid, as a dry cleaning fluid, as a polymerization medium, as a document preservation medium, as a heat transfer agent, as a cell size regulator for use in foam blowing, as a heat transfer agent for use in vapor phase soldering, and as a metal working agent in the cutting or forming of metals. At least some of the HFEs exhibit unexpectedly high thermal stabilities, making them particularly useful in high temperature applications. Thus, at least some embodiments of the invention meet the above-described, ongoing need for HFEs that can meet the performance requirements of a variety of different applications (as well as the need for efficient and cost-effective processes for their preparation).

In another aspect, this invention provides fluorochemical diketone compounds useful as starting materials in preparing the hydrofluoroether compounds of the invention. Such fluorochemical ketone compounds comprise two terminal, branched fluoroalkylcarbonyl or perfluoroalkylcarbonyl groups that optionally comprise at least one catenated heteroatom selected from divalent ether oxygen atoms and trivalent nitrogen atoms (preferably, perfluoroalkylcarbonyl groups that optionally comprise at least one catenated heteroatom selected from divalent ether oxygen atoms and trivalent nitrogen atoms) and an intervening linear or branched (preferably, branched) perfluoroalkylene segment having only 2 or 3 in-chain atoms, the perfluoroalkylene segment optionally containing a catenated heteroatom selected from a divalent ether oxygen atom and a trivalent nitrogen atom, with the proviso that the perfluoroalkylene segment is branched when it does not contain a catenated heteroatom, and wherein the branching of the terminal fluoroalkylcarbonyl or perfluoroalkylcarbonyl groups is at the carbon atom of the group's fluoroalkyl or perfluoroalkyl moiety that is adjacent to the group's carbonyl moiety.

In yet another aspect, this invention also provides a process for preparing the hydrofluoroether compounds comprising (a) reacting at least one fluorochemical ketone compound with at least one fluoride source to form at least one fluorochemical alkoxide, the fluorochemical ketone compound comprising two terminal, branched fluoroalkylcarbonyl or perfluoroalkylcarbonyl groups that optionally comprise at least one catenated heteroatom selected from divalent ether oxygen atoms and trivalent nitrogen atoms (preferably, perfluoroalkylcarbonyl groups that optionally comprise at least one catenated heteroatom selected from divalent ether oxygen atoms and trivalent nitrogen atoms) and an intervening linear or branched (preferably, linear) perfluoroalkylene segment, the perfluoroalkylene segment optionally containing one or more catenated heteroatoms selected from divalent ether oxygen atoms and trivalent nitrogen atoms, wherein the branching of the terminal fluoroalkylcarbonyl or perfluoroalkylcarbonyl groups is at the carbon atom of the group's fluoroalkyl or perfluoroalkyl moiety that is adjacent to the group's carbonyl moiety; and (b) reacting the fluorochemical alkoxide with at least one alkylating agent to form at least one hydrofluoroether compound.

In still other aspects, this invention provides the following processes for using the hydrofluoroether compounds of the invention:

A process for removing a contaminant (for example, an oil or grease, a particulate, or water) from an article comprising contacting the article with a composition comprising at least one hydrofluoroether compound of the invention.

A process for preparing a foamed plastic comprises vaporizing a blowing agent mixture in the presence of at least one foamable polymer or the precursors of at least one foamable polymer, the blowing agent mixture comprising at least one hydrofluoroether compound of the invention.

A process for vapor phase soldering comprising melting solder by immersing at least one component that comprises solder in a body of fluorochemical liquid vapor that comprises at least one hydrofluoroether compound of the invention.

A process for transferring heat comprising transferring heat between a heat source and a heat sink through the use of a heat transfer agent comprising at least one hydrofluoroether compound of the invention.

A process for depositing a coating on a substrate comprising applying to at least a portion of at least one surface of the substrate a composition comprising (a) a solvent composition comprising at least one hydrofluoroether compound of the invention; and (b) at least one coating material (for example, a fluorochemical polyether or a document preservation material) that is soluble or dispersible in the solvent composition.

A process for metal, cermet, or composite working comprising applying a working fluid to a metal, cermet, or composite workpiece and tool, the working fluid comprising at least one hydrofluoroether compound of the invention and at least one lubricious additive.

A polymerization process comprising polymerizing at least one monomer (preferably, a fluorine-containing monomer) in the presence of at least one polymerization initiator and at least one hydrofluoroether compound of the invention.

DETAILED DESCRIPTION

Definitions

As used in this patent application:

"catenated heteroatom" means an atom other than carbon (for example, oxygen, nitrogen, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Hydrofluoroether Compounds

The novel compounds of the invention comprise at least one (preferably, one or two) five- or six-membered, perfluorinated heterocyclic ring(s), each ring comprising four or five ring carbon atoms and one or two catenated (that is, in-chain) heteroatoms selected from divalent ether oxygen atoms and trivalent nitrogen atoms, at least one of the catenated heteroatoms being a divalent ether oxygen atom, and each of the ring carbon atoms adjacent to the divalent ether oxygen atom bearing a fluorochemical group that comprises a tetrafluoroethylidene moiety (—($CF_3$)CF—) that is directly bonded to the ring carbon atom, the fluorochemical group optionally comprising at least one catenated heteroatom selected from divalent ether oxygen atoms and trivalent nitrogen atoms.

Preferably, one of the ring carbon atoms that bears a fluorochemical group further bears a fluorine atom, and the other further bears an alkoxy or fluoroalkoxy group or, when a second (or higher) ring is present, a divalent oxyalkyleneoxy or oxyfluoroalkyleneoxy group that is bonded to a ring carbon atom of the second (or higher) ring. More preferably, the remaining ring carbon atoms (that is, those that are not adjacent to the divalent ether oxygen atom) can be independently unsubstituted (bearing only fluorine) or perfluoroalkyl-monosubstituted (bearing a fluorine atom and a perfluoroalkyl group that optionally contains at least one catenated heteroatom).

The rings of the hydrofluoroether compound are preferably identical. Preferably, each ring comprises only one catenated heteroatom, and/or each fluorochemical group is a branched perfluoroalkyl group that optionally comprises at least one catenated heteroatom selected from divalent ether oxygen atoms and trivalent nitrogen atoms. More preferably, the hydrofluoroether compound comprises only one ring, and/or the branched perfluoroalkyl group optionally comprises at least one catenated divalent ether oxygen atom (most preferably, the branched perfluoroalkyl group is a hexafluoroisopropyl group).

Two classes of the compounds of the invention are those that can be represented by the following general formulas (I) and (II):

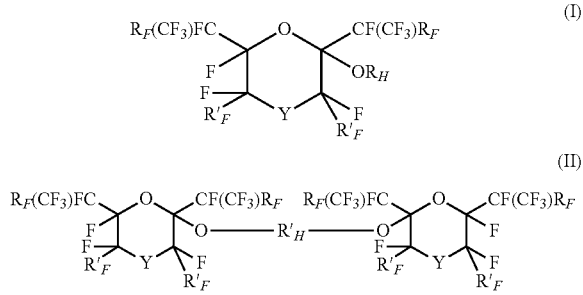

wherein each $R_F$ is independently a linear or branched perfluoroalkyl group that optionally contains at least one catenated heteroatom selected from divalent ether oxygen atoms and trivalent nitrogen atoms and that optionally comprises a terminal moiety selected from —$CF_2H$, —$CFHCF_3$, and —$CF_2OCH_3$ (preferably, a linear or branched perfluoroalkyl group that has from one to about six carbon atoms and that optionally contains at least one catenated heteroatom selected from divalent ether oxygen atoms and trivalent nitrogen atoms; more preferably, a linear or branched perfluoroalkyl group that has from one to about three carbon atoms and that optionally contains at least one catenated divalent ether oxygen atom; most preferably, a perfluoromethyl group); each $R_F'$ is independently a fluorine atom or a perfluoroalkyl group that is linear or branched and that optionally contains at least one catenated heteroatom (preferably, having from one to about four carbon atoms and/or no catenated heteroatoms); Y is a covalent bond, —O—, —$CF(R_F')$—, or —$N(R_F'')$—, wherein $R_F''$ is a perfluoroalkyl group that is linear or branched and that optionally contains at least one catenated heteroatom (preferably, having from one to about four carbon atoms and/or no catenated heteroatoms); $R_H$ is an alkyl or fluoroalkyl group that is linear, branched, cyclic, or a combination thereof and that optionally contains at least one catenated heteroatom (preferably, linear or branched and/or having from one to about eight carbon atoms and/or no catenated heteroatoms); and $R_H'$ is an alkylene or fluoroalkylene group that is linear, branched, cyclic, or a combination thereof, that has at least two carbon atoms, and that optionally contains at least one catenated heteroatom (preferably, linear or branched and/or having from two to about eight carbon atoms and/or having at least four hydrogen atoms and/or no catenated heteroatoms).

More preferably, each $R_F'$ is independently a fluorine atom or a perfluoromethyl group; Y is a covalent bond or a perfluoromethylene group; $R_H$ is an alkyl group having from one to about four carbon atoms; and $R_H'$ is an alkylene group having from two to about four carbon atoms. Most preferably, each $R_F'$ is a fluorine atom; Y is a covalent bond; $R_H$ is an ethyl group; and $R_H'$ is a propylene group. The compounds of Formula (I) are generally preferred.

Representative examples of the hydrofluoroether compounds of the invention include the following, where an "F" in the center of a ring structure indicates that all ring substituents that are not explicitly shown are fluorine:

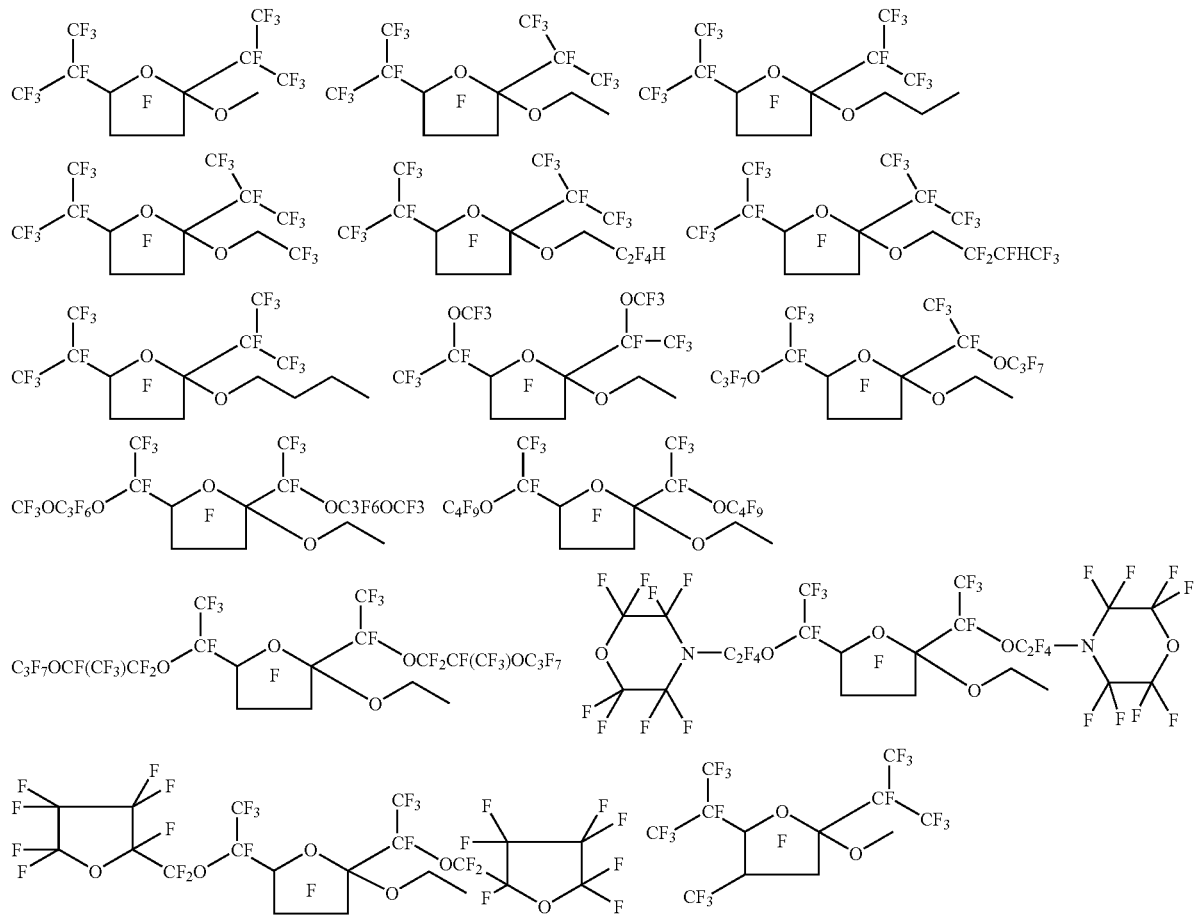

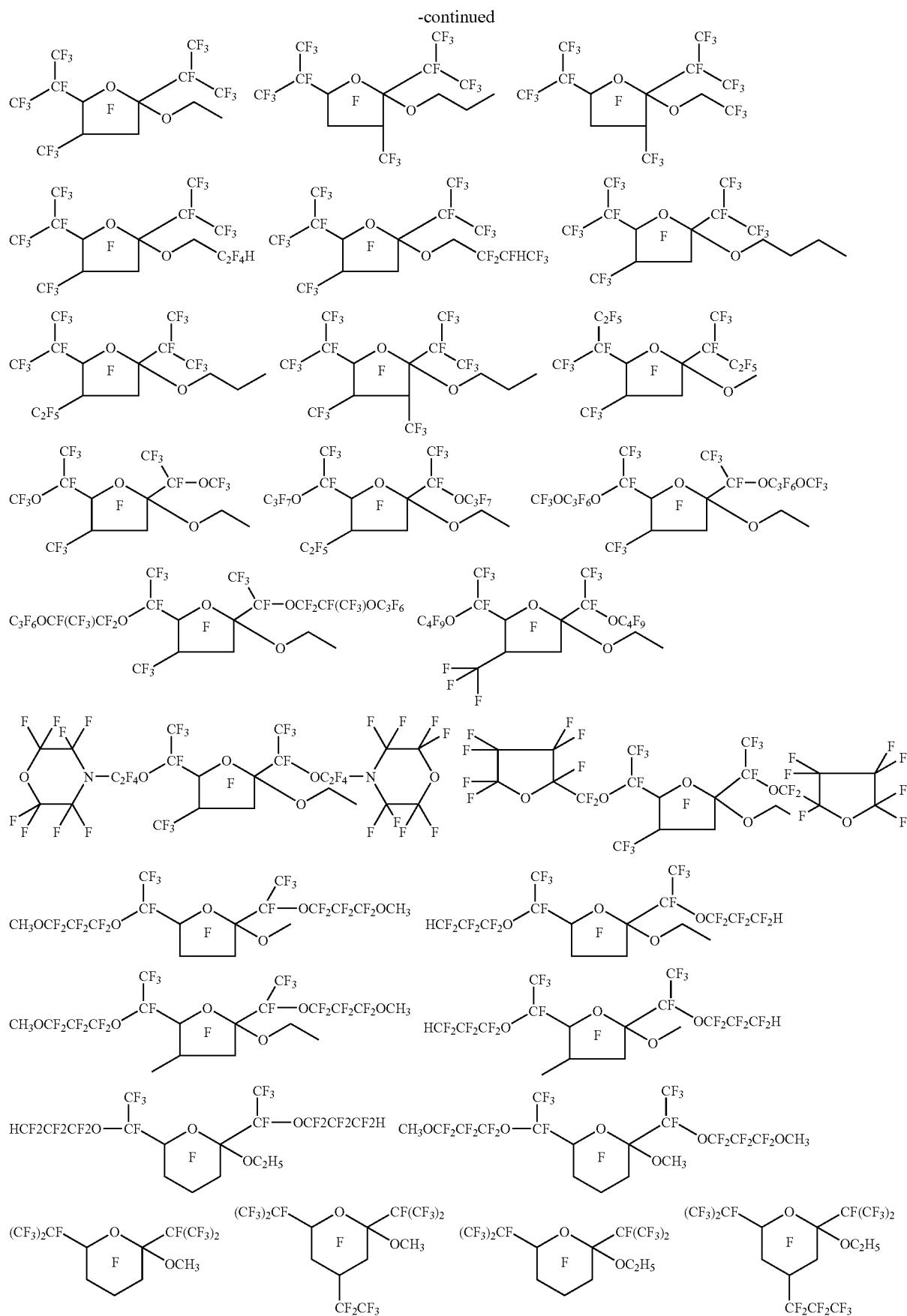

-continued
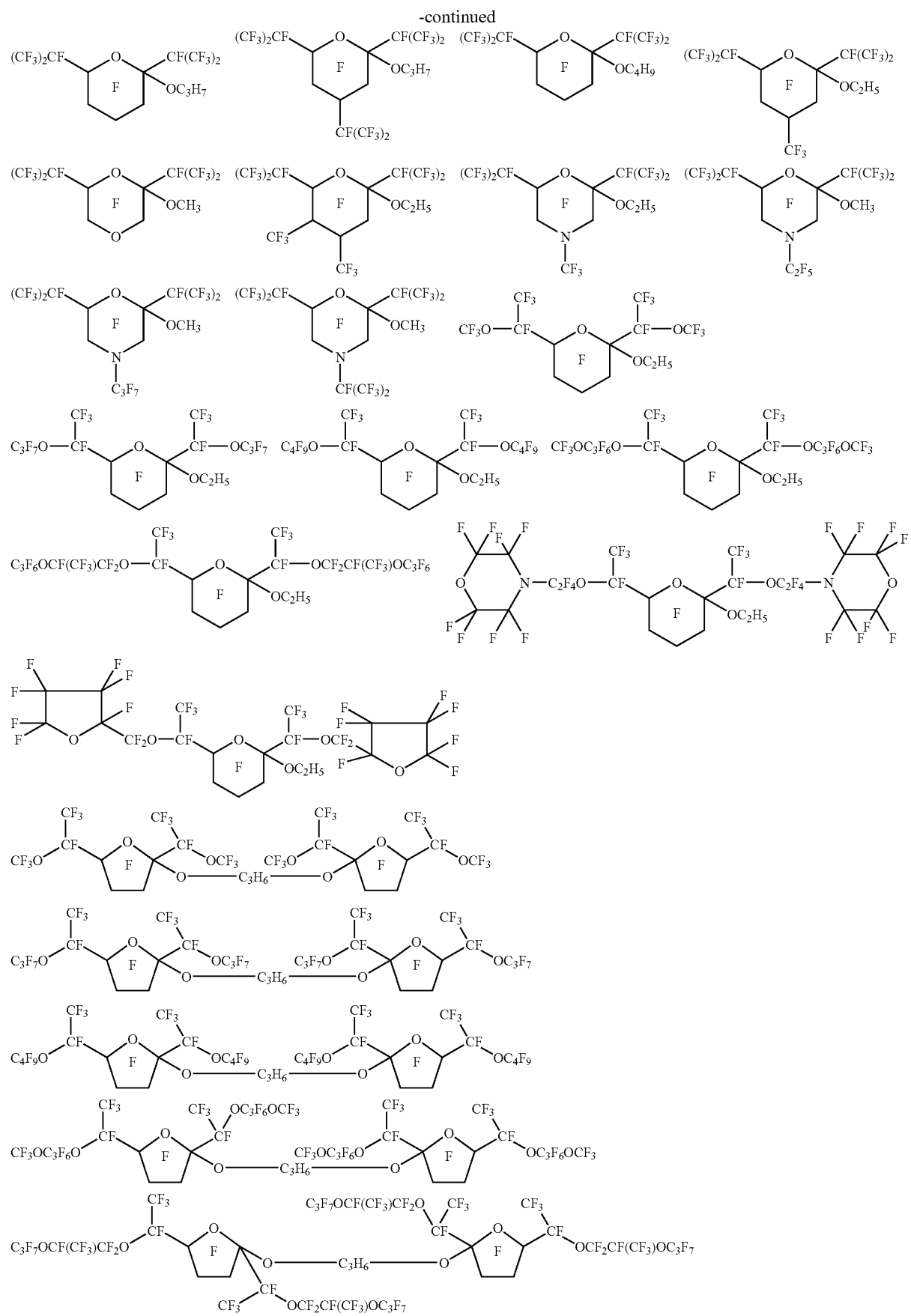

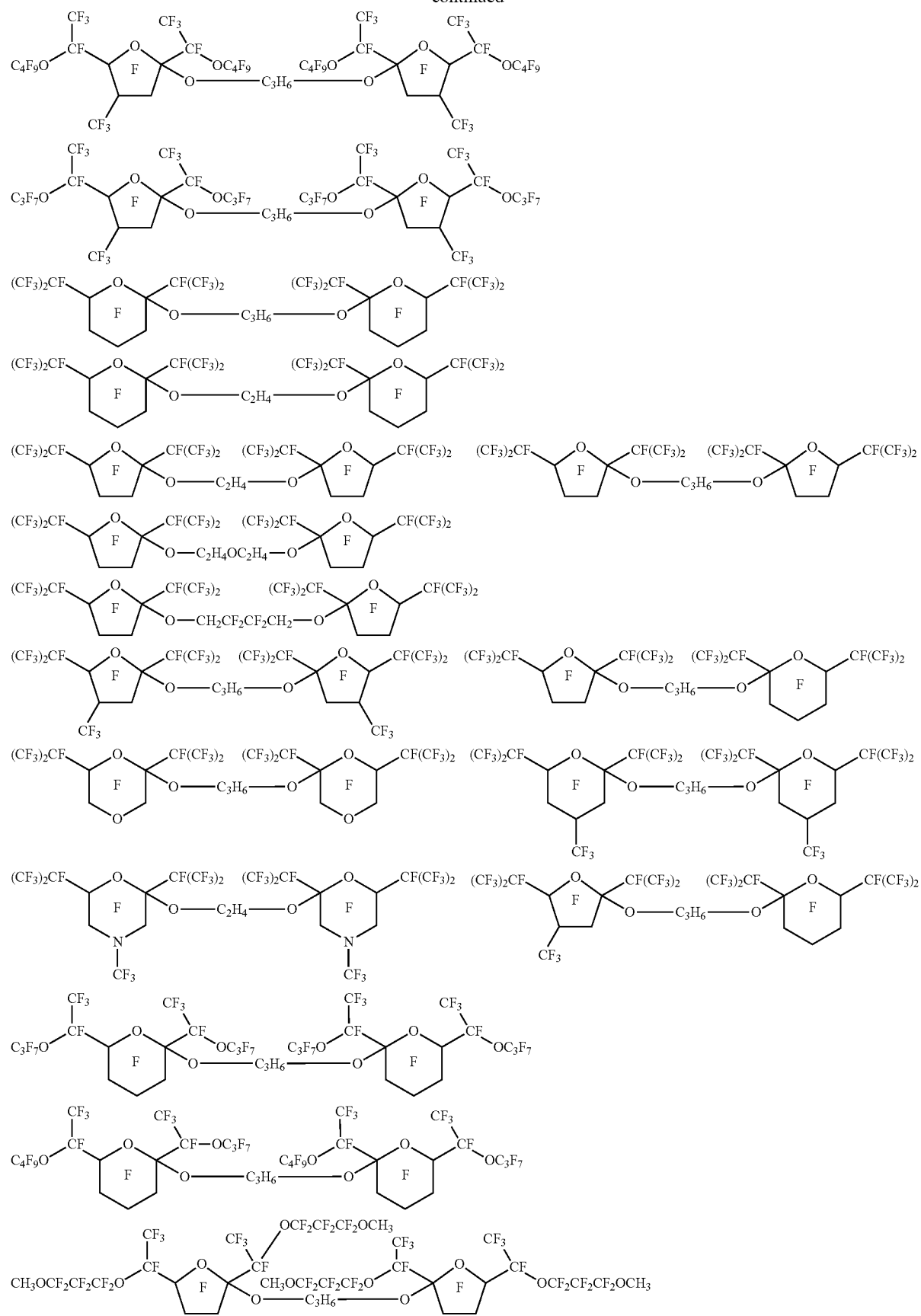

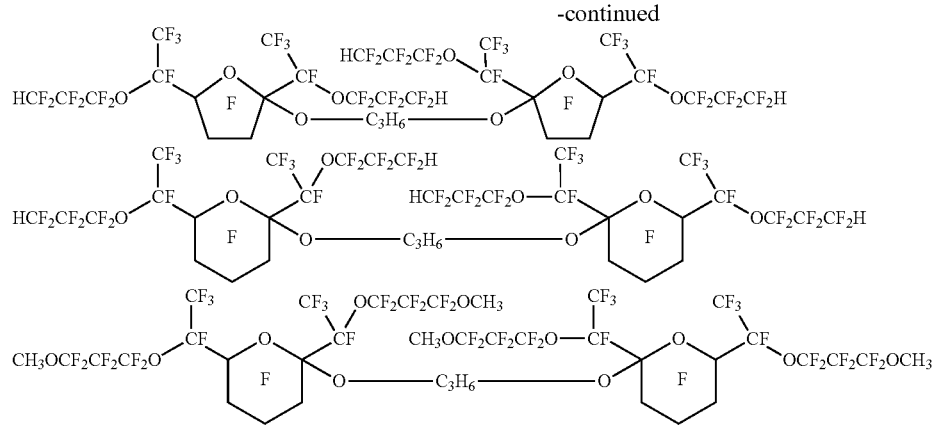
and the like, and mixtures thereof.
Preferred hydrofluoroether compounds include
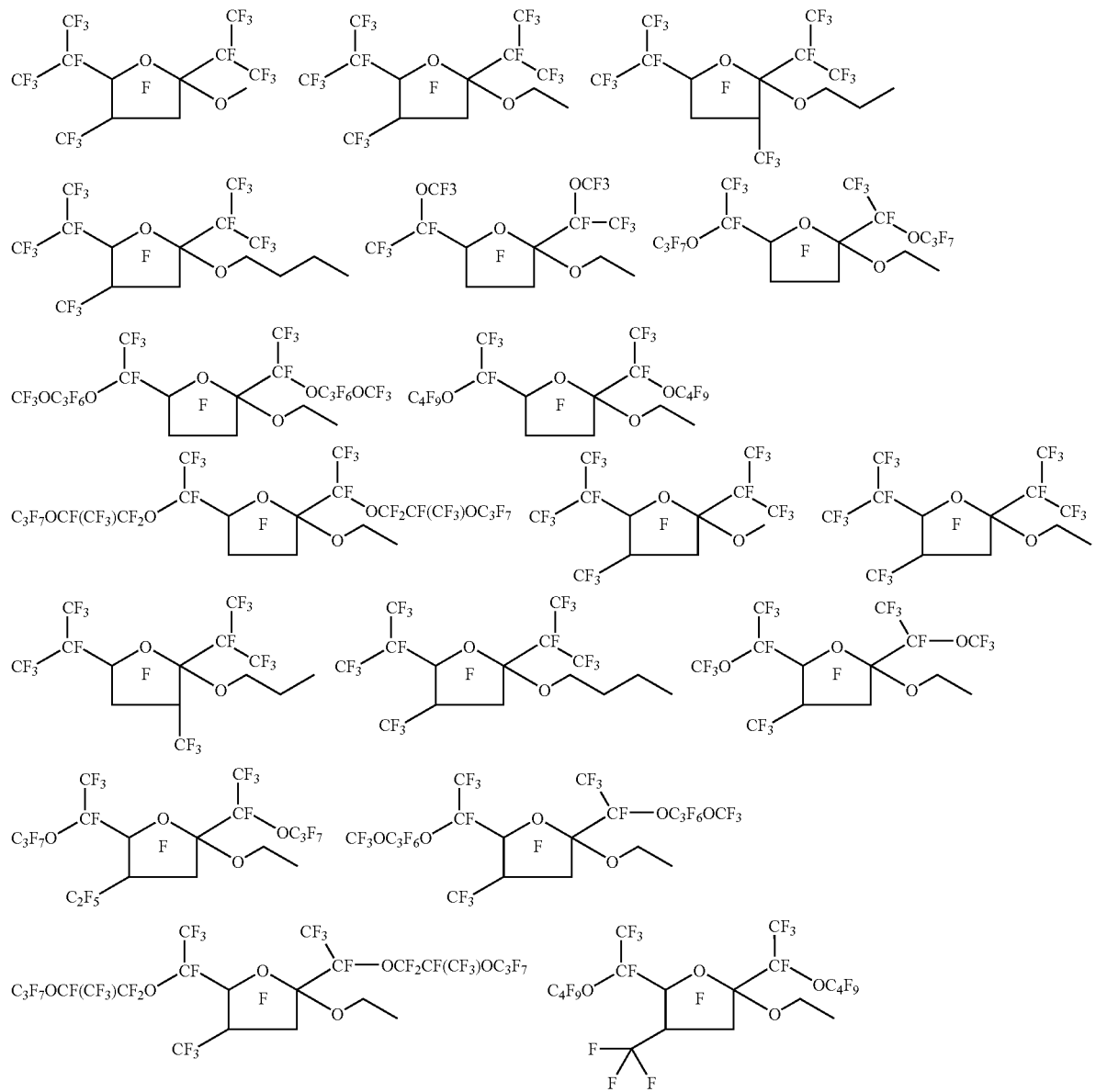

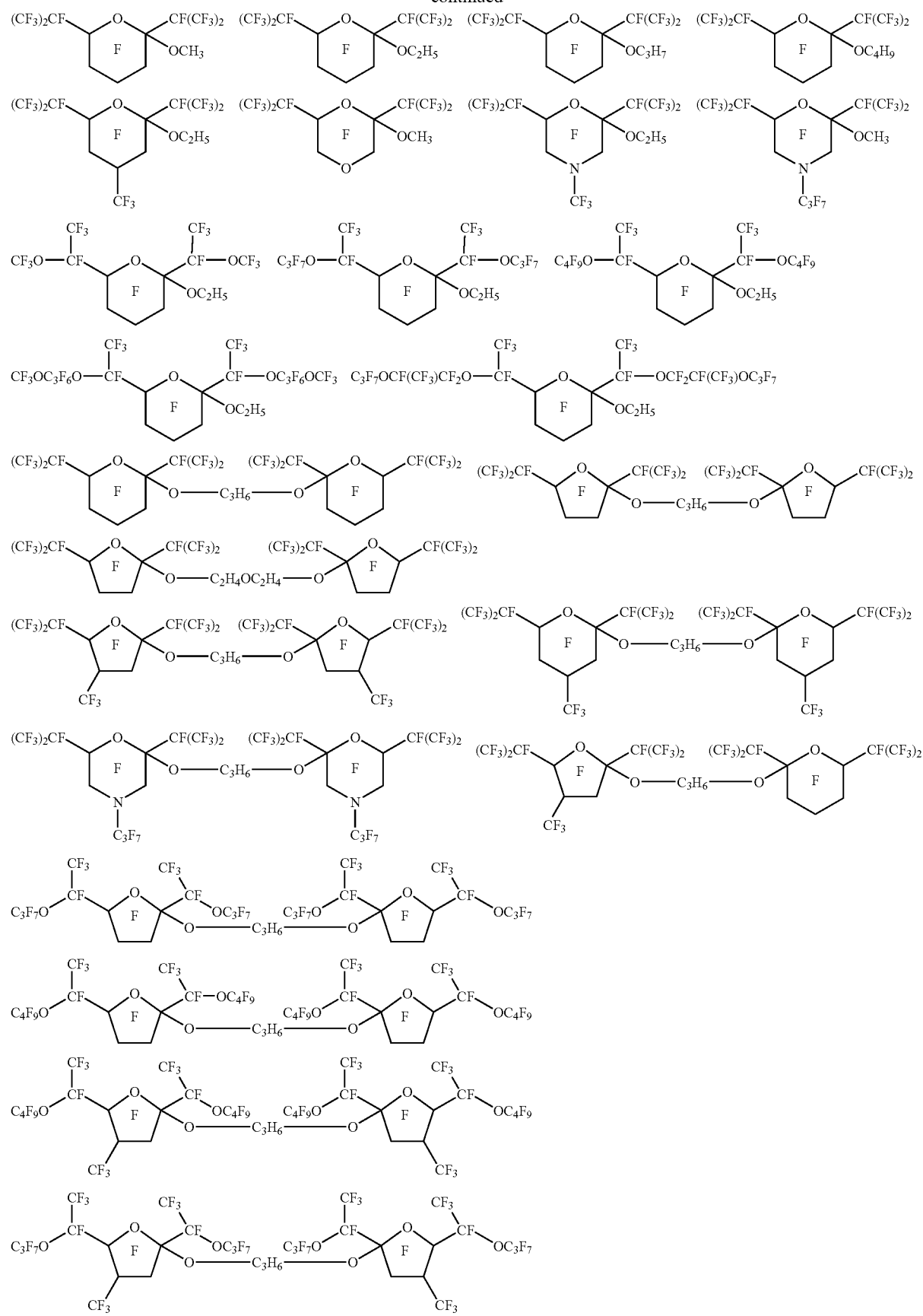

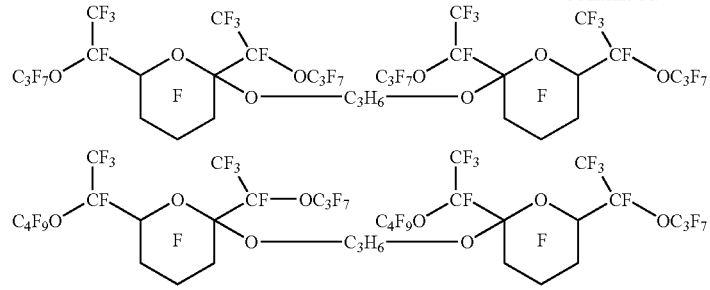
and mixtures thereof, with
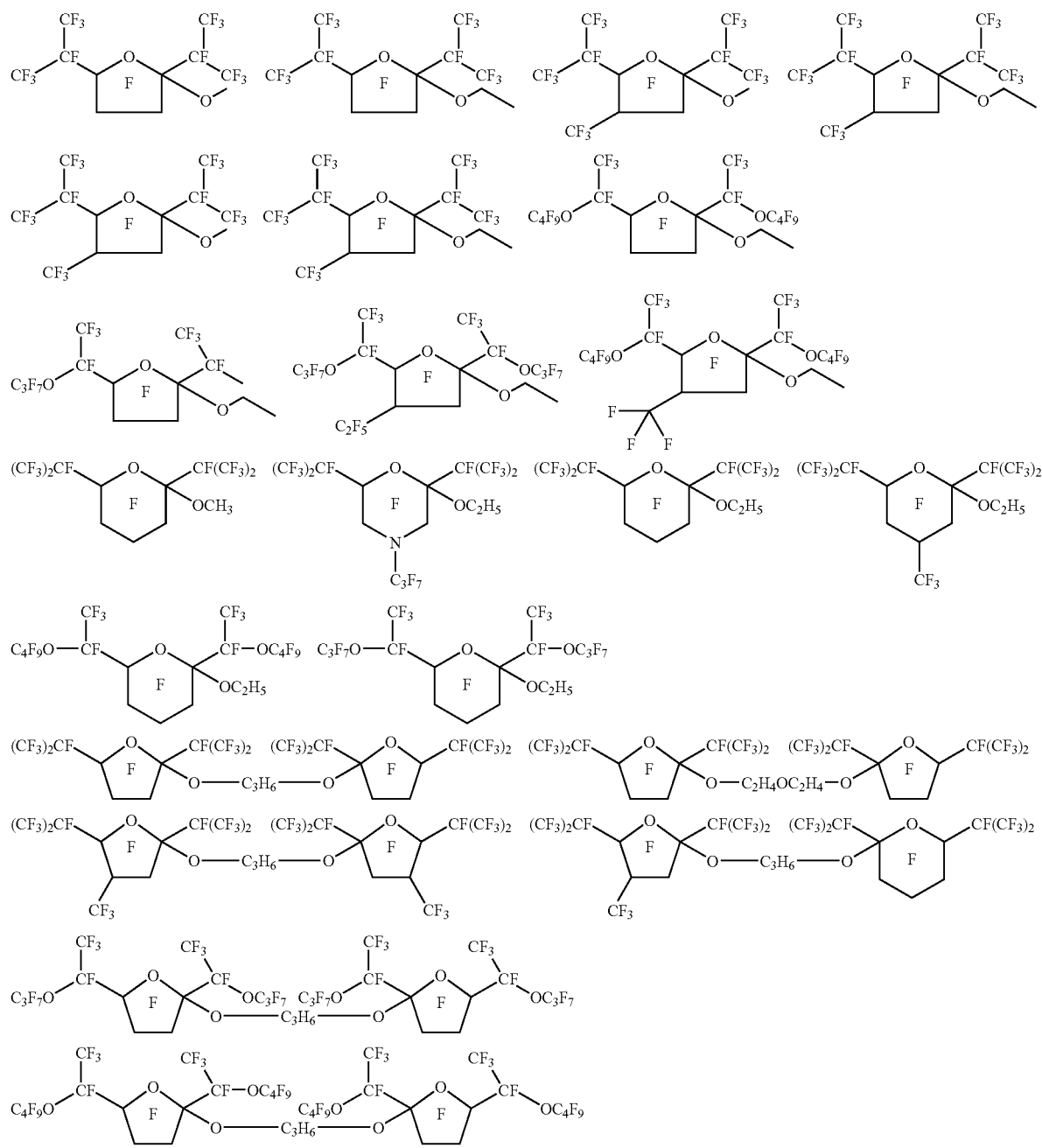

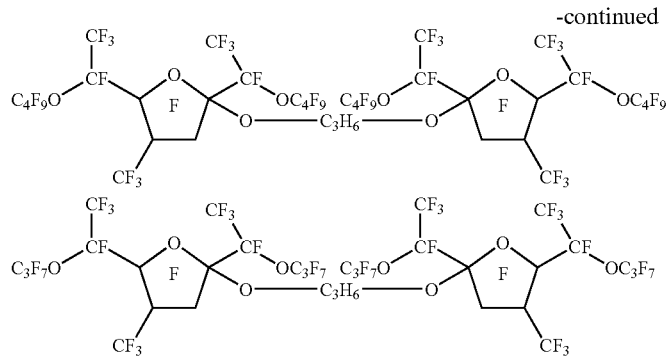

and mixtures thereof being more preferred.

The hydrofluoroether compounds of the invention are hydrophobic and less oleophobic than their perfluoroether analogs, relatively chemically unreactive, thermally stable, water insoluble, and they can be made in accordance with this invention in high yield, high purity, and with a wide range of molecular weights. Their covalent carbon-hydrogen bonds are generally degradable by atmospheric photo-oxidation, thus making the hydrofluoroether compounds environmentally acceptable or compatible.

Preparation of Hydrofluoroether Compounds

The hydrofluoroether compounds (HFEs) of the invention can be prepared by the alkylation of fluorochemical alkoxides prepared by the reaction of a fluorochemical ketone (more specifically, a fluorochemical diketone having (a) branched fluoroalkylcarbonyl or perfluoroalkylcarbonyl endgroups that optionally comprise at least one catenated heteroatom selected from divalent ether oxygen atoms and trivalent nitrogen atoms, and (b) an intervening linear or branched perfluoroalkylene segment) with an anhydrous alkali metal fluoride (for example, potassium fluoride or cesium fluoride) or anhydrous silver fluoride (preferably, in an anhydrous polar, aprotic solvent). Preferably, the perfluoroalkylene segment has two or three in-chain atoms. See, for example, the preparative methods described in French Patent Publication No. 2,287,432 and German Patent Publication No. 1,294,949, as well as the method described in detail in U.S. Pat. No. 5,750,797 (Vitcak et al.), the description of which is incorporated herein by reference.

The starting fluorochemical diketone compounds can be prepared from the corresponding fluorochemical diacyl fluorides by combining at least one fluorochemical diacyl fluoride with at least one perfluoroolefin (for example, hexafluoropropene) or fluoro- or perfluorovinyl ether in the presence of at least one anhydrous fluoride source (for example, anhydrous potassium fluoride) and at least one anhydrous, polar, aprotic solvent (for example, diglyme (that is, diethylene glycol dimethyl ether or bis(2-methoxy)ethyl ether)). A phase transfer catalyst can be utilized, if desired.

For example, a fluorochemical diacyl fluoride, an anhydrous fluoride source (generally a catalytic amount), a solvent, and, optionally, a phase transfer catalyst (generally a catalytic amount) can be combined in any order in any suitable reactor (for example, a metal reactor; preferably, a pressure reactor), which can then be sealed and heated to a desired reaction temperature (for example, about 75° C.) under autogenous pressure. At least a stoichiometric amount (up to a stoichiometric excess of one hundred percent or more) of perfluoroolefin or fluoro- or perfluorovinyl ether can then be added to the reactor (or can be added continuously or in portions), generally with stirring or agitation of the reactor contents and, preferably, with temperature control.

After completion of perfluoroolefin or fluoro- or perfluorovinyl ether addition, or after the reaction has run to completion, the reactor can be cooled and vented and the contents purified by any suitable separation method. For example, the resulting reaction mixture can be filtered (for example, to remove the fluoride source), phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting diketone product).

The fluorochemical diacyl fluorides (used for preparing the starting fluorochemical diketones) can be prepared from, for example, the corresponding hydrocarbon diacyl fluorides or diacyl chlorides (the latter of which are commercially available) or certain lactones, anhydrides, or dimethyl esters by electrochemical fluorination in anhydrous hydrogen fluoride or by direct fluorination using elemental fluorine.

Perfluoroolefins that are useful in preparing the starting fluorochemical diketones include those that contain at least one carbon atom bonded to one of the carbon atoms of the olefinic double bond. Such perfluoroolefins provide fluorochemical ketone compounds that are generally characterized by the presence of terminal branched perfluoroalkylcarbonyl groups.

The perfluoroolefins can be prepared by any of a variety of standard synthetic procedures that are well-known in the art. Some perfluoroolefins (for example, $CF_3CF{=}CF_2$, $C_5F_{11}CF{=}CF_2$, and $C_2F_5CF{=}CF_2$) are also commercially available (for example, from Synquest or from Apollo Scientific, Ltd.).

Representative examples of perfluoroolefins that are useful include $CF_3CF{=}CF_2$, $C_3F_7CF{=}CF_2$, $C_5F_{11}CF{=}CF_2$, $CF_3CF_2CF{=}CF_2$, and the like, and mixtures thereof. (Mixtures can be used, if desired, but mixtures are generally less preferred due to the resulting production of product mixtures that can require purification.) $CF_3CF{=}CF_2$ is preferred.

Fluoro- and perfluorovinyl ethers that are useful in carrying out the preparation process include those that possess a terminal perfluorovinyl group. Such fluoro- and perfluorovinyl ether starting compounds, which optionally can further contain one or more catenated heteroatoms (in addition to the ether oxygen of the fluoro- and perfluorovinyl ethers), can be prepared by the reaction of a fluorochemical acid fluoride or a fluorochemical ketone with hexafluoropropylene oxide (HFPO) to form an intermediate branched acid fluoride adduct. This adduct can then be reacted with a base to form an intermediate carboxylic acid salt, which can then be decarboxylated at elevated temperature (optionally, in the presence of an inert solvent). Some perfluorovinyl ethers (for example, perfluorovinyl ethers such as $C_3F_7OCF=CF_2$, $C_3F_7OCF(CF_3)CF_2OCF=CF_2$, and $CF_3OCF=CF_2$) are also commercially available (for example, from Synquest or from Apollo Scientific, Ltd.).

Representative examples of fluoro- and perfluorovinyl ethers that are useful in preparing the hydrofluoroether compounds include $C_3F_7OCF=CF_2$, $C_3F_7OCF(CF_3)CF_2OCF=CF_2$, $CF_3OCF=CF_2$, $C_4F_9OCF=CF_2$, $CF_3OC_3F_6OCF=CF_2$, $C_2F_5OCF=CF_2$, $(CF_3)_2CFCF_2OCF=CF_2$, $C_5F_{11}OCF=CF_2$, $HCF_2CF_2CF_2OCF=CF_2$, $CH_3OCF_2CF_2CF_2OCF=CF_2$, $CF_3CFHCF_2CF_2OCF=CF_2$,

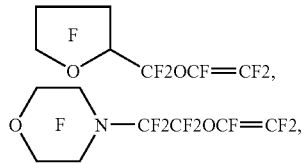

and the like, and mixtures thereof. Preferred vinyl ethers include $C_3F_7OCF=CF_2$, $C_4F_9OCF=CF_2$, $CF_3OC_3F_6OCF=CF_2$, and mixtures thereof. $C_3F_7OCF=CF_2$, $C_4F_9OCF=CF_2$, and mixtures thereof are more preferred. (Mixtures of starting compounds can be used, if desired, but mixtures are generally less preferred due to the resulting production of product mixtures that can require purification.)

Suitable anhydrous fluoride sources include anhydrous fluorine-containing compounds that can dissociate to provide an anhydrous source of fluoride ion. Such compounds include metal fluorides (for example, potassium fluoride, rubidium fluoride, cesium fluoride, and the like, and mixtures thereof), metal bifluorides, quaternary ammonium fluorides, quaternary phosphonium fluorides, and the like, and mixtures thereof. Preferred anhydrous fluoride sources include potassium fluoride, cesium fluoride, and mixtures thereof; with potassium fluoride being more preferred.

Suitable solvents include anhydrous, polar, aprotic solvents such as glycol ether solvents (for example, glyme, diglyme, triglyme, tetraglyme, and the like, and mixtures thereof), tetrahydrofuran, dimethylformamide, dimethyl sulfoxide, sulfolane, acetonitrile, and the like, and mixtures thereof. Preferred solvents include glyme, diglyme, triglyme, tetraglyme, dimethylformamide, and mixtures thereof; with glyme, diglyme, dimethylformamide, and mixtures thereof being more preferred and diglyme most preferred.

Suitable phase transfer catalysts include quaternary ammonium salts, quaternary phosphonium salts, crown ethers, cryptands, and the like, and mixtures thereof. Preferred salt counter ions include those that are commercially available (for example, chloride), as well as those such as monoalkyl sulfates, monoalkyl sulfonates, and the like, and mixtures thereof. Useful crown ethers include 4'-aminobenzyl-15-crown-5, 1-aza-12-crown-5, 1-aza-15-crown-5, 1-aza-18-crown-5, bis[(benzo-15-crown-5)-15-ylmethyl]pimelate, dicyclohexano-18-crown-6, 4'-formylbenzo-15-crown-5, 2-(hydroxymethyl)-15-crown-5, 4'-nitrobenzo-15-crown-5, poly[(dibenzo-18-crown-6)-coformaldehyde], and the like, and mixtures thereof. Useful commercially available cryptands include KRYPTOFIX 21, 211, 222, and 222b (available from Sigma-Aldrich Chemical Company, Milwaukee, Wis.). Preferred catalysts are quaternary ammonium salts, due to their relative abundance and cost effectiveness. Useful commercially available quaternary ammonium salts include ADOGEN 464 (a methyltrialkyl($C_8$-$C_{10}$) ammonium chloride available from Sigma-Aldrich Chemical Company). Another preferred phase transfer catalyst is $(C_8H_{17})_3N^+CH_3^-OSO_3CH_3$, which can be prepared by reaction of trioctylamine with dimethylsulfate. If utilized, phase transfer catalyst is typically added at a concentration constituting between about 0.001 mol percent and about 5.0 mol percent of the reaction mixture.

In preparing the hydrofluoroether compounds of the invention, a fluorochemical diketone, an anhydrous fluoride source (generally a stoichiometric excess), an alkylating agent (generally a stoichiometric excess), a solvent, and, optionally, a phase transfer catalyst (generally a catalytic amount) can be combined in any order in any suitable reactor (for example, a metal reactor; preferably, a pressure reactor). The reactor can then be sealed and heated to a desired reaction temperature (for example, about 30-50° C.) under autogenous pressure for a period sufficient to achieve a desired level of conversion (for example, for about 16-72 hours), generally with stirring or agitation of the reactor contents and, preferably, with temperature control.

After the reaction has run to completion, the reactor can be cooled and vented and the contents purified by any suitable separation method. For example, the resulting reaction mixture can be filtered (for example, to remove the fluoride source), phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting HFE product).

Alternatively, after the reactor is cooled, the reactor contents can be treated with aqueous potassium hydroxide followed by an additional heating period (for example, 60° C. for about 1-3 hours) to react with and remove the excess alkylating agent. The resulting reaction mixture can then be purified as described above or, alternatively, can be subjected to steam distillation with separation of the resulting lower fluorochemical phase of the resulting distillate and further purification by, for example, fractional distillation.

Suitable (and preferred) anhydrous fluoride sources and phase transfer catalysts for use in preparing the hydrofluoroether compounds of the invention include those described above. Suitable starting fluorochemical diketone compounds include
$(CF_3)_2CFC(O)C_2F_4C(O)CF(CF_3)_2$
$CF_3OCF(CF_3)C(O)C_2F_4C(O)CF(CF_3)OCF_3$
$C_3F_7OCF(CF_3)C(O)C_2F_4C(O)CF(CF_3)OC_3F_7$
$C_4F_9OCF(CF_3)C(O)C_2F_4C(O)CF(CF_3)OC_4F_9$
$CF_3OC_3F_6OCF(CF_3)C(O)C_2F_4C(O)CF(CF_3)OC_3F_6OCF_3$
$C_3F_7OCF(CF_3)CF_2OCF(CF_3)C(O)C_2F_4C(O)CF(CF_3)OCF_2CF(CF_3)OC_3F_7$
$(CF_3)_2CFC(O)CF(CF_3)CF_2C(O)CF(CF_3)_2$
$CF_3OCF(CF_3)C(O)CF(CF_3)CF_2C(O)CF(CF_3)OCF_3$
$C_3F_7OCF(CF_3)C(O)CF(CF_3)CF_2C(O)CF(CF_3)OC_3F_7$
$C_4F_9OCF(CF_3)C(O)CF(CF_3)CF_2C(O)CF(CF_3)OC_4F_9$
$CF_3OC_3F_6OCF(CF_3)C(O)CF(CF_3)CF_2C(O)CF(CF_3)OC_3F_6OCF_3$
$C_3F_7OCF(CF_3)CF_2OCF(CF_3)C(O)CF(CF_3)CF_2C(O)CF(CF_3)OCF_2CF(CF_3)OC_3F_7$
$(CF_3)_2CFC(O)CF(C_2F_5)CF_2C(O)CF(CF_3)_2$
$C_3F_7OCF(CF_3)C(O)CF(C_2F_5)CF_2C(O)CF(CF_3)OC_3F_7$
$C_4F_9OCF(CF_3)C(O)CF(C_2F_5)CF_2C(O)CF(CF_3)OC_4F_9$ $(CF_3)_2CFC(O)CF(CF_3)CF(CF_3)C(O)CF(CF_3)_2$
$(CF_3)_2CFC(O)CF_2CF_2CF_2C(O)CF(CF_3)_2$
$CF_3OCF(CF_3)C(O)CF_2CF_2CF_2C(O)CF(CF_3)OCF_3$
$C_3F_7OCF(CF_3)C(O)CF_2CF_2CF_2C(O)CF(CF_3)OC_3F_7$
$C_4F_9OCF(CF_3)C(O)CF_2CF_2CF_2C(O)CF(CF_3)OC_4F_9$
$CF_3OC_3F_6OCF(CF_3)C(O)CF_2CF_2CF_2C(O)CF(CF_3)OC_3F_6OCF_3$
$C_3F_7OCF(CF_3)CF_2OCF(CF_3)C(O)CF_2CF_2CF_2C(O)CF(CF_3)OCF_2CF(CF_3)OC_3F_7$
$(CF_3)_2CFC(O)CF_2CF(CF_3)CF_2C(O)CF(CF_3)_2$
$CF_3OCF(CF_3)C(O)CF_2CF(CF_3)CF_2C(O)CF(CF_3)OCF_3$
$C_3F_7OCF(CF_3)C(O)CF_2CF(CF_3)CF_2C(O)CF(CF_3)OC_3F_7$
$C_4F_9OCF(CF_3)C(O)CF_2CF(CF_3)CF_2C(O)CF(CF_3)OC_4F_9$
$CF_3OC_3F_6OCF(CF_3)C(O)CF_2CF(CF_3)CF_2C(O)CF(CF_3)OC_3F_6OCF_3$
$C_3F_7OCF(CF_3)CF_2OCF(CF_3)C(O)CF_2CF(CF_3)CF_2C(O)CF(CF_3)OCF_2CF(CF_3)OC_3F_7$
$(CF_3)_2CFC(O)CF_2CF(C_2F_5)CF_2C(O)CF(CF_3)_2$
$(CF_3)_2CFC(O)CF_2CF(C_3F_7)CF_2C(O)CF(CF_3)_2$
$C_4F_9OCF(CF_3)C(O)CF_2CF(C_3F_7)CF_2C(O)CF(CF_3)OC_4F_9$
$(CF_3)_2CFC(O)CF_2CF[CF(CF_3)_2]CF_2C(O)CF(CF_3)_2$
$(CF_3)_2CFC(O)CF(CF_3)CF(CF_3)CF_2C(O)CF(CF_3)_2$
$(CF_3)_2CFC(O)CF_2OCF_2C(O)CF(CF_3)_2$
$(CF_3)_2CFC(O)CF_2N(CF_3)CF_2C(O)CF(CF_3)_2$
$CF_3OCF(CF_3)C(O)CF_2N(CF_3)CF_2C(O)CF(CF_3)OCF_3$
$C_3F_7OCF(CF_3)C(O)CF_2N(CF_3)CF_2C(O)CF(CF_3)OC_3F_7$
$C_4F_9OCF(CF_3)C(O)CF_2N(CF_3)CF_2C(O)CF(CF_3)OC_4F_9$
$CF_3OC_3F_6OCF(CF_3)C(O)CF_2N(CF_3)CF_2C(O)CF(CF_3)OC_3F_6OCF_3$
$C_3F_7OCF(CF_3)CF_2OCF(CF_3)C(O)CF_2N(CF_3)CF_2C(O)CF(CF_3)OCF_2CF(CF_3)OC_3F_7$
$(CF_3)_2CFC(O)CF_2N(C_2F_5)CF_2C(O)CF(CF_3)_2$
$(CF_3)_2CFC(O)CF_2N(C_3F_7)CF_2C(O)CF(CF_3)_2$
$(CF_3)_2CFC(O)CF_2N[CF(CF_3)_2]CF_2C(O)CF(CF_3)_2$
$CH_3OCF_2CF_2CF_2OCF(CF_3)C(O)C_2F_4C(O)CF(CF_3)OCF_2CF_2CF_2OCH_3$
$CH_3OCF_2CF_2CF_2OCF(CF_3)C(O)CF(CF_3)CF_2C(O)CF(CF_3)OCF_2CF_2CF_2OCH_3$
$CH_3OCF_2CF_2CF_2OCF(CF_3)C(O)CF_2CF_2CF_2C(O)CF(CF_3)OCF_2CF_2CF_2OCH_3$
$HCF_2CF_2CF_2OCF(CF_3)C(O)C_2F_4C(O)CF(CF_3)OCF_2CF_2CF_2H$
$HCF_2CF_2CF_2OCF(CF_3)C(O)CF(CF_3)CF_2C(O)CF(CF_3)OCF_2CF_2CF_2H$
$HCF_2CF_2CF_2OCF(CF_3)C(O)CF_2CF_2CF_2C(O)CF(CF_3)OCF_2CF_2CF_2H$

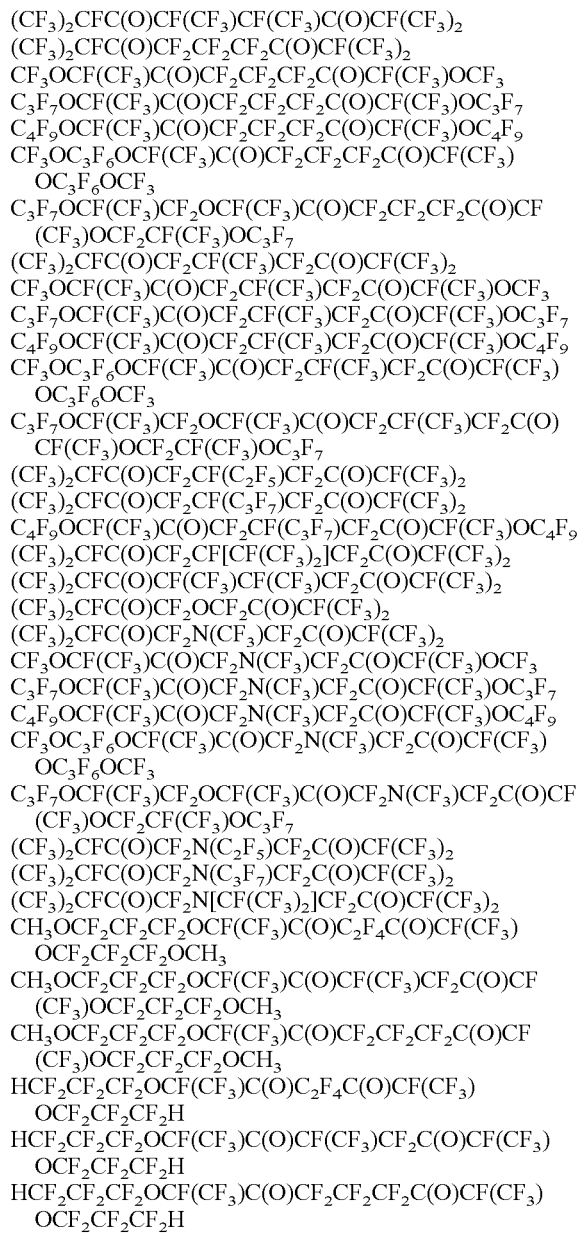

and the like, and mixtures thereof.

Suitable alkylating agents include dialkyl sulfates (for example, dimethyl sulfate); alkyl halides (for example, methyl iodide); alkyl p-toluenesulfonates (for example, methyl p-toluenesulfonate); alkyl perfluoroalkanesulfonates (for example, methyl perfluoromethanesulfonate); fluoroalkyl perfluoroalkanesulfonates (for example, 2,2,2-trifluoroethyl perfluorobutanesulfonate); difunctional alkylating agents including di-tosylates (for example, 1,3-propanediol di-p-toluenesulfonate), di-mesylates (for example, 1,4-butanediol bis(methanesulfonate)), and bis(perfluoroalkanesulfonates) (for example, 1,3-propanediol bis(nonafluorobutanesulfonate)); and the like; and mixtures thereof. Preferred alkylating agents include dialkyl sulfates and mixtures thereof.

Suitable (and preferred) polar, aprotic solvents include those described above, as well as acyclic ethers such as diethyl ether, ethylene glycol dimethyl ether, and diethylene glycol dimethyl ether; carboxylic acid esters such as methyl formate, ethyl formate, and methyl acetate; carbonate esters such as diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and the like; and mixtures thereof.

Use of Hydrofluoroether Compounds

The hydrofluoroether compounds of the invention (or a normally liquid composition comprising, consisting, or consisting essentially thereof) can be used in various applications. For example, the compounds can be used as solvents for precision or metal cleaning of electronic articles such as disks or circuit boards; as heat transfer agents (for example, for hybrid vehicle cooling and for the cooling or heating of integrated circuit tools in the semiconductor industry, including tools such as dry etchers, integrated circuit testers, photolithography exposure tools (steppers), ashers, chemical vapor deposition equipment, automated test equipment (probers), and physical vapor deposition equipment (sputterers)); as cell size regulators in making foam insulation (for example, polyurethane, phenolic, and thermoplastic foams); as carrier fluids or solvents for document preservation materials and for lubricants; as power cycle working fluids such as for heat pumps; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists when used with, for example, a chlorohydrocarbon such as 1,1,1-trichloroethane or trichloroethylene.

The hydrofluoroether compounds typically exhibit high dielectric strengths (for example, greater than about $10^8$ ohm-cm), which can make them well-suited for use in the semiconductor industry. The hydrofluoroether compounds that exhibit unexpectedly high thermal stabilities can be particularly useful in high temperature applications such as in heat transfer applications in the semiconductor industry and in flat screen panel manufacture.

The hydrofluoroether compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents can be chosen to modify or enhance the properties of a composition for a particular use and can be utilized in ratios (of co-solvent(s) to hydrofluoroether(s)) such that the resulting composition preferably has no flash point. If desired, the hydrofluoroether compounds can be used in combination with other compounds that are very similar in properties relative to a particular use (for example, other hydrofluoroether compounds) to form compositions that "consist essentially" of the hydrofluoroether compounds of the invention.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The hydrofluoroether compounds are useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.), the descriptions of which are incorporated herein. Both organic and inorganic substrates can be cleaned by contacting them with a composition comprising at least one HFE of the invention. Most contaminants can be removed, including hydrocarbon contaminants, fluorocarbon contaminants, particulates, and water.

In using the compounds for the drying of or displacing water from the surface of articles (such as circuit boards), the process of drying or water displacement described in, for example, U.S. Pat. No. 5,125,978 (Flynn et al.) can be used. Broadly, such process comprises contacting the surface of an article with a liquid composition comprising at least one hydrofluoroether compound of the invention, preferably in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978, which description is incorporated herein.

In using the compounds of the invention in vapor phase soldering, the process described in, for example, U.S. Pat. No. 5,104,034 (Hansen) can be used, which description is incorporated herein. Briefly, such process comprises immersing a component to be soldered in a body of vapor comprising at least one hydrofluoroether compound of this invention to melt the solder. In carrying out such a process, a liquid pool of a hydrofluoroether composition is heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the compounds of the invention as cell size regulators in making plastic foam (such as foamed polyurethane), the process reactants and reaction conditions described in, for example, U.S. Pat. No. 5,210,106 (Dams et al.) and U.S. Pat. No. 5,539,008 (Dams et al.) can be used, which descriptions are incorporated herein. One such process comprises vaporizing a blowing agent mixture in the presence of at least one foamable polymer or the precursors of at least one foamable polymer, the blowing agent mixture comprising at least one hydrofluoroether compound of the invention.

In using the compounds of the invention as heat transfer agents, the processes described in, for example, U.S. Reissue Pat. No. 37,119 E (Sherwood) and U.S. Pat. No. 6,374,907 B1 (Tousignant et al.) can be used, which descriptions are incorporated herein. In carrying out such processes, heat is transferred between a heat source (for example, a silicon wafer or a component of a flat panel display) and a heat sink through the use of a heat transfer agent comprising at least one hydrofluoroether compound of the invention. Unlike some HFEs that are used as heat transfer agents, the HFEs of the invention are not mixtures of components of widely disparate molecular weights. Rather, the HFEs are generally monodisperse (that is, of a single molecular weight). This means that their physical properties remain relatively constant over time, thereby avoiding significant heat transfer performance deterioration. In addition, the HFEs of the invention generally exhibit a wide liquid range, useful viscosity over that range, and relatively high thermal stability at end use temperatures, making them well-suited for use as heat transfer fluids.

In using the hydrofluoroether compounds of the invention as deposition solvents in coating applications or in document preservation applications, the processes described in, for example, U.S. Pat. No. 5,925,611 (Flynn et al.) and U.S. Pat. No. 6,080,448 (Leiner et al.) can be used, which descriptions are incorporated herein. Such processes for depositing a coating on a substrate (for example, magnetic recording media or cellulose-based materials) comprises applying, to at least a portion of at least one surface of the substrate, a composition comprising (a) a solvent composition comprising at least one hydrofluoroether compound of the invention; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Preferred materials include perfluoropolyether, hydrocarbon, and silicone lubricants; amorphous copolymers of tetrafluoroethylene; polytetrafluoroethylene; document preservation materials; and combinations thereof. Most preferably, the material is a perfluoropolyether lubricant or a document preservation material.

In using the hydrofluoroether compounds of the invention in cutting or abrasive working operations, the processes described in, for example, U.S. Pat. No. 6,759,374 (Milbrath et al.) can be used, the descriptions of which are incorporated herein. Such a process for metal, cermet, or composite working comprises applying a working fluid to a metal, cermet, or composite workpiece and tool, the working fluid comprising at least one hydrofluoroether compound of the invention and at least one lubricious additive. The working fluid can further comprise one or more conventional additives (for example, corrosion inhibitors, antioxidants, defoamers, dyes, bactericides, freezing point depressants, metal deactivators, co-solvents, and the like, and mixtures thereof).

In using the hydrofluoroether compounds of the invention as polymerization media or as chain transfer agents, the processes described in, for example, Research Disclosures, Number 40576, page 81 (January 1998) and in U.S. Pat. No. 5,182,342 (Feiring et al.) and U.S. Pat. No. 6,399,729 (Farnham et al.) can be used, the descriptions of which are incorporated herein. Such processes comprise polymerizing at least one monomer (preferably, at least one fluorine-containing monomer) in the presence of at least one polymerization initiator and at least one hydrofluoroether compound of the invention.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, St. Louis, Mo. unless otherwise noted.

In the following examples, mixtures of diastereomers were obtained due to the presence of two (or more) optical centers in the molecules. These diastereomers had boiling points that were very close together, and thus the diastereomers were not separated by distillation. In some cases, however, such diastereomers can be easily separated by gas chromatography.

Test Methods

Nuclear Magnetic Resonance (NMR)

$^1$H and $^{19}$F NMR spectra were run on a Varian UNITYplus 400 Fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Gas Chromatography (GC)

GC samples were run on a Hewlett Packard 6890 Series Gas Chromatograph, obtainable from Agilent Technologies, Palo Alto, Calif.

Infrared (IR) Spectroscopy

IR spectra were run on a THERMO-NICOLET, Avatar 370 Fourier Transform Infrared (FTIR) Spectrometer (obtainable from Thermo Electron Corporation, Waltham, Mass.).

| Table of Abbreviations | |
|---|---|
| Abbreviation or Trade Designation | Description |
| b.p. | Boiling point, measured at ambient pressure unless otherwise specified |

Materials

Potassium Fluoride: Obtained from Sigma Aldrich Company, St. Louis, Mo. Spray-dried, stored in a 125° C. oven, and ground using mortar and pestle just before use.

Anhydrous Diglyme (anhydrous diethylene glycol dimethyl ether): Obtained from Sigma Aldrich Company, St. Louis, Mo.

Adogen™ 464 phase transfer catalyst (methyltrialkyl ($C_8$-$C_{10}$) ammonium chloride, 49 percent (%) solution in anhydrous diglyme): Obtained from Sigma Aldrich Company, St Louis, Mo. Used typically as a diglyme solution containing Adogen™ 464, purified by fractional distillation to remove isopropyl alcohol.

Hexafluoropropene (HFP): Obtained from Dyneon, St. Paul, Minn.

Diethylsulfate: Obtained from Sigma Aldrich Company, St. Louis, Mo.

Dipropylsulfate: Obtained from Sigma Aldrich Company, St. Louis, Mo.

Potassium Hydroxide: Obtained from Sigma Aldrich Company, St. Louis, Mo.

Magnesium Sulfate: Obtained from Sigma Aldrich Company, St Louis, Mo.

Di-n-propylsulfate: Obtained from TCI America, Portland, Oreg.

1,3-Propanediol di-p-tosylate: Obtained from Sigma Aldrich Company, St. Louis, Mo.

Dimethyl methyl succinate: Obtained from Sigma-Aldrich Company, St. Louis, Mo.

Novec™ HFE-7100 fluid (hydrofluoroether): Obtained from 3M Company, St. Paul, Minn.

Perfluoropropylvinyl ether ($C_3F_7OCF=CF_2$); Obtained from Dyneon, St. Paul, Minn. or Synquest Laboratories, Alachua, Fla.

Tetrafluorosuccinyl Fluoride ($FCOC_2F_4COF$) Intermediate: Tetrafluorosuccinyl fluoride was prepared by electrochemical fluorination (ECF) of butyrolactone in a Simons ECF cell essentially of the type described in U.S. Pat. No. 2,713,593 (Brice et al.) and by R. E. Banks in *Preparation and Industrial Applications of Organofluorine Compounds*, pages 19-43, Halsted Press, New York (1982). The resulting gaseous products from the cell were further purified by fractional distillation to yield about 83% tetrafluorosuccinyl fluoride as well as some other fluorinated acid fluorides and inert materials. This mixture was used in subsequent reactions without further purification.

Hexafluoroglutaryl Fluoride ($FCO(CF_2)_3COF$) Intermediate: Hexafluoroglutaryl fluoride was prepared by electrochemical fluorination of glutaric anhydride followed by fractional distillation essentially as described above for tetrafluorosuccinyl fluoride intermediate. This yielded essentially 100% of a number of isomers of which the linear isomer was the primary product, and this mixture was used in subsequent reactions without further purification. As used herein, the term "perfluoroglutaryl fluoride" will refer to this mixture.

Perfluoromethylsuccinyl Fluoride ($FC(O)CF(CF_3)CF_2C(O)F$) Intermediate: Perfluoromethylsuccinyl fluoride was prepared by the electrochemical fluorination of dimethyl methylsuccinate followed by fractional distillation essentially as described above for the tetrafluorosuccinyl fluoride intermediate. The resulting material contained about 63.3% of perfluoromethylsuccinyl fluoride and 9.5% of hexafluoroglutaryl fluoride, as well as some other inert materials. This mixture was used in subsequent reactions without further purification. As used herein, the term "perfluoromethylsuccinyl fluoride" will refer to this mixture.

Dodecafluoro-2,7-trifluoromethyl-3,6-octadione (($CF_3)_2CFCOC_2F_4COCF(CF_3)_2$) Intermediate: This intermediate was prepared as follows: A clean, dry, 600 mL, stainless steel, Parr pressure reactor (obtained from Parr Instrument Company, Moline, Ill.) was charged with 23.2 grams (0.40 moles) spray-dried potassium fluoride, 130 grams anhydrous diglyme, and 15.0 grams (0.016 moles) Adogen™ 464 phase transfer catalyst (diglyme solution containing 50.4 weight % catalyst). The reactor was sealed, brought to a vacuum of 0.03 atmospheres, and then isolated from the vacuum system, cooled with a dry-ice acetone bath, charged with 191 grams (0.91 moles) perfluorosuccinyl fluoride, and then heated to 80° C. with agitation. 292 grams (1.95 moles) of hexafluoropropene was added over a 4 hour period, and the resulting reaction was allowed to run for 16 hours. At the end of the 16 hours, the mixture was cooled to room temperature and transferred to a 500 mL round bottom flask and vacuum distilled (at 0.05 atmospheres). The two resulting phases of the distillate were separated to afford a 78% molar yield based on perfluorosuccinyl fluoride. The material was purified using a 10 perforated plate internal bellows column to 98.3% purity.

$(CF_3)_2CFC(O)CF(CF_3)CF_2C(O)CF(CF_3)_2$ and $(CF_3)_2CFC(O)CF_2CF_2CF_2C(O)CF(CF_3)_2$ Intermediates: These intermediates were prepared as follows: A clean, dry, 600 mL, stainless steel, Parr pressure reactor was charged with 9.0 grams (0.15 moles) spray-dried potassium fluoride and 138 grams anhydrous diglyme. The reactor was sealed, cooled with a dry-ice acetone bath to about −50° C., evacuated, and charged with 135 grams (0.40 moles) perfluoromethylsuccinyl fluoride. The reactor was then heated to 75° C. with agitation, and 144 grams (0.96 moles) of hexafluoropropene was added over a period of about 8 hours. The reactor was held at 75° C. and agitated an additional 16 hours. The reactor was cooled, excess pressure vented, opened, and the reactor contents added to a separatory funnel. The resulting lower fluorochemical phase was separated to provide 181 grams, which was fractionated on a concentric tube column to provide 115 grams of greater than 99% pure diketones.

$C_3F_7OCF(CF_3)COC_2F_4COF$ and $C_3F_7OCF(CF_3)COC_2F_4COCF(CF_3)OC_3F_7$ Intermediates: These intermediates were prepared as follows: A clean, dry, 600 mL, stainless steel, Parr pressure reactor was charged with 5.1 grams (0.088 moles) spray-dried potassium fluoride, 238 grams anhydrous diglyme, 8.3 grams Adogen™ 464 phase transfer catalyst (diglyme solution containing 49 weight percent catalyst), and 150.8 grams (0.57 moles) perfluoropropylvinyl ether. The reactor was sealed, brought to a vacuum of about 0.006579 atmospheres, and then isolated from the vacuum system, cooled with a dry-ice acetone bath to about −18° C., and charged with 54 grams (0.28 moles) perfluorosuccinyl fluoride. The reactor was then heated to 75° C. with agitation over a period of about 48 hours. The reactor was then cooled, opened, and the solid potassium fluoride removed by filtration through cheesecloth. The resulting lower fluorochemical phase was separated and distilled (distillation range of 120-145° C., about 87 percent purity of the mono-adduct (1:1 addition product)). The residue in the distillation vessel was the bis-adduct (distillation range greater than 182° C., $C_3F_7OCF(CF_3)COC_2F_4COCF(CF_3)OC_3F_7$, purity of 96 percent). IR spectra showed a COF band at 1883.2 cm$^{-1}$, as well as a CO stretch at 1782.1 cm$^{-1}$ for the mono-adduct and 1779.2 cm$^{-1}$ for the bis-adduct.

Example 1

Preparation of 2-ethoxy-3,3,4,4-tetrafluoro-2,5-bis-(1,2,2,2-tetrafluoro-1-trifluoromethylethyl)tetrahydrofuran

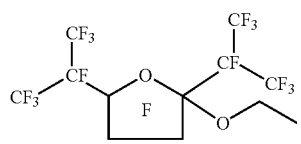

A 500 mL round bottom flask, equipped with an overhead stirrer, heating mantle, thermocouple temperature control, nitrogen bubbler, and condenser was charged with 32.3 grams (0.56 moles) spray-dried potassium fluoride, 104 grams anhydrous diglyme, 12.7 grams (0.014 moles) Adogen™ 464 phase transfer catalyst, 89.1 grams (0.58 moles) diethyl sulfate, and 220 grams (0.445 moles) 98.3% pure dodecafluoro-2,7-trifluoromethyl-3,6-octadione. The flask was maintained at 54° C. for 16 hours and then allowed to cool down. After cooling to 25° C., 50 grams (0.40 moles) aqueous potassium hydroxide (45% solution in water) and 75 grams water were added to the flask. The resulting solution was heated to 80° C. and held for 4 hours and the resulting crude product isolated by steam distillation and washed two times with equal weights of water to obtain 2-ethoxy-3,3,4,4-tetrafluoro-2,5-bis-(1,2,2,2-tetrafluoro-1-trifluoromethylethyl)tetrahydrofuran at 82 mole % yield with a purity of 96.7%. Purification to 98.6% was accomplished by vacuum fractional distillation. GCMS and $^{19}$F-NMR confirmed the desired product.

Example 2

Preparation of 2-propoxy-3,3,4,4-tetrafluoro-2,5-bis-(1,2,2,2-tetrafluoro-1-trifluoromethylethyl)tetrahydrofuran

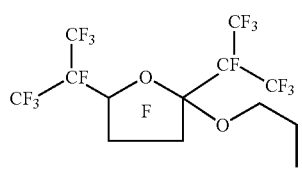

Example 2 was carried out using essentially the same procedure and process as those described in Example 1, except that the diethyl sulfate charge was replaced with dipropyl sulfate at the same mole ratio relative to dodecafluoro-2,7-trifluoromethyl-3,6-octadione, and the mole ratio of Adogen™ 464 phase transfer catalyst was increased to 0.036.

The alkylation yield was 85%. The resulting material was purified by fractional distillation to 97.1%, b.p. 185° C. at ambient pressure (about 0.97 atmospheres). The product structure was confirmed by GCMS and $^{19}$F NMR.

Example 3

Preparation of 2-methoxy-3,3,4,4-tetrafluoro-2,5-bis-(1,2,2,2-tetrafluoro-1-trifluoromethylethyl)tetrahydrofuran

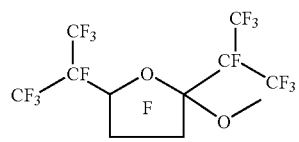

A clean, dry, 600 mL stainless steel, Parr pressure reactor was charged with 42.7 grams (0.74 moles) potassium fluoride, 196 grams diglyme, and 121 grams of 75.7% pure (0.47 moles) perfluorosuccinyl fluoride and heated to 70° C. 208 grams (1.39 moles) hexafluoropropene was added to the reactor over a 4 hour period, and the resulting reaction was allowed to run for one additional hour. At the end of one hour, the reactor was cooled to less than 0° C. using a dry ice-acetone bath, opened, and further charged with 26.6 grams (0.027 moles) Adogen™ 464 phase transfer catalyst and 73.2 grams (0.58 moles) dimethyl sulfate. The reactor was sealed again, agitated, and heated to 32° C. for 17 hours. 50 grams (0.40 moles) aqueous potassium hydroxide (45% solution in water) and 30 grams water were pressurized into the reactor from a separate cylinder, and the reaction was allowed to run for another 24 hours at 32° C. The resulting reaction mixture was transferred to a 1 L round bottom flask, with the addition of water used to rinse the reactor. The resulting crude product was steam distilled and then washed two times with equal weights of water to provide 2-methoxy-3,3,4,4-tetrafluoro-2,5-bis-(1,2,2,2-tetrafluoro-1-trifluoromethylethyl)tetrahydrofuran at 76 mole % yield relative to perfluorosuccinyl fluoride, with an 87% purity. The resulting product was purified by distillation to 95.4% with a b.p. of 170° C. The product structure was confirmed by GCMS and $^{19}$F NMR.

Example 4

Preparation of 2,3,3,4,4,5,5-Heptafluoro-6-methoxy-2,6-bis-(1,2,2,2-tetrafluoro-1-trifluoromethylethyl)tetrahydropyran

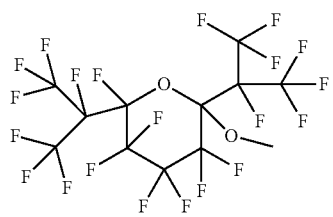

Example 4 was carried out using essentially the same process and conditions as those described in Example 3, except hexafluoroglutaryl fluoride was used instead of perfluorosuccinyl fluoride. A 39% alkylation yield was obtained. The resulting material was purified by fractional distillation to a purity of 90%. The resulting product containing three isomers of the desired material was confirmed by GCMS.

Example 5

Preparation of 2,3,3,4,4,5,5-Heptafluoro-6-ethoxy-2,6-bis-(1,2,2,2-tetrafluoro-1-trifluoromethylethyl)tetrahydropyran

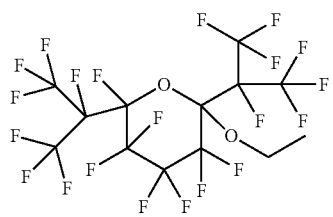

Example 5 was carried out in essentially the same manner as Example 3 as follows: A clean, dry, 600 mL, stainless steel, Parr pressure reactor was charged with 36.3 grams (0.625 moles) spray-dried potassium fluoride, 174 grams diglyme, and 122 grams (0.50 moles) perfluoroglutaryl fluoride and was heated to 80-85° C. with agitation. 172.5 grams (1.15 moles) hexafluoropropene was added to the resulting mixture over an 8 hour period, and the mixture was held at 80° C. for an additional 16 hours. At the end of the 16 hours, the reactor was cooled to 25° C., opened up, and charged with 14.3 grams (0.0155 moles) Adogen™ 464 phase transfer catalyst and 106.3 grams (0.69 moles) diethyl sulfate. Then the reactor was sealed again and heated with agitation to 54° C. for 72 hours. 50 grams (0.40 moles) aqueous 45% potassium hydroxide and 50 grams of water were added to the reactor by using a charge cylinder and held for 24 hours at 65° C. The resulting reaction mixture was transferred to a 1 L round bottom flask along with several water rinses of the reactor, followed by steam distillation. The resulting product was separated from the upper aqueous phase and washed twice with water to obtain 2,3,3,4,4,5,5-heptafluoro-6-ethoxy-2,6-bis-(1,2,2,2-tetrafluoro-1-trifluoromethylethyl)tetrahydropyran at 29 mole % yield relative to perfluoroglutaryl fluoride, with a purity of 77%. The product was confirmed by GCMS to contain 3 isomers of the desired material.

Example 6

Reaction of $(CF_3)_2CFC(O)CF(CF_3)CF_2C(O)CF(CF_3)_2$ and $(CF_3)_2CFC(O)CF_2CF_2CF_2C(O)CF(CF_3)_2$ with diethyl sulfate A 1 L round bottom flask was charged with 115.0 grams (0.21 moles) of the isomer mixture $(CF_3)_2CFC(O)CF(CF_3)CF_2C(O)CF(CF_3)_2$ and $(CF_3)_2CFC(O)CF_2CF_2CF_2C(O)CF(CF_3)_2$ prepared essentially as described above, 33 grams (0.57 moles) potassium fluoride, 11 grams (0.024 moles) Adogen™ 464 phase transfer catalyst (diglyme solution containing 50 weight % catalyst), 88.0 grams (0.57 moles) diethyl sulfate, and 182 grams of diglyme as solvent. The temperature of the flask was set to 52° C., and the resulting mixture was stirred for 2 days. The resulting reaction was quenched with 88 grams distilled water and 106 grams 45% KOH, and the resulting mixture was subjected to steam distillation. The mixture was distilled using a concentric tube column (b.p.=189° C.). The structures shown below were verified by GCMS and NMR.

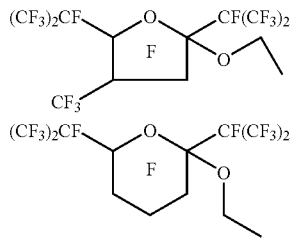

Example 7

Reaction of $(CF_3)_2CFC(O)CF(CF_3)CF_2C(O)CF(CF_3)_2$ and $(CF_3)_2CFC(O)CF_2CF_2CF_2C(O)CF(CF_3)_2$ with di-n-propyl sulfate A 2 L round bottom flask was charged with 231.6 grams (0.43 moles) of the isomer mixture $(CF_3)_2CFC(O)CF(CF_3)CF_2C(O)CF(CF_3)_2$ and $(CF_3)_2CFC(O)CF_2CF_2CF_2C(O)CF(CF_3)_2$ prepared essentially as described above, 30 grams (0.51 moles) potassium fluoride, 11 grams (0.024 moles) Adogen™ 464 phase transfer catalyst (diglyme solution containing 50 weight % catalyst), 93.9 grams (0.52 moles) di-n-propyl sulfate, and 400 mL of diglyme as solvent. The temperature of the flask was set to 75° C., and the resulting mixture was stirred for 3 days. The resulting reaction was quenched with 200 mL distilled water, and the resulting mixture steam distilled from the pot. The mixture was distilled using a concentric tube column (b.p.=196-198° C.) to provide 55 grams with a purity of 99.9% of the isomers of the desired product. The structures shown below were verified by GCMS and NMR.

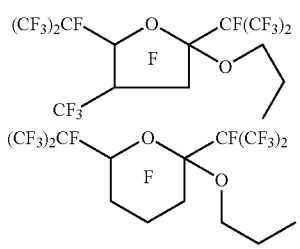

Example 8

Reaction of $(CF_3)_2CFCOC_2F_4COCF(CF_3)_2$ with 1,3-propanediol ditosylate

A clean, dry, 600 ml, stainless steel Parr pressure reactor was charged with 12.8 grams (0.22 moles) spray-dried potassium fluoride, 200 mL anhydrous diglyme, 6.6 grams Adogen™ 464 phase transfer catalyst (diglyme solution containing 49 weight % catalyst), 74.4 grams (0.14 moles) of 95% $(CF_3)_2CFC(O)C_2F_4C(O)CF(CF_3)_2$, and 25 grams (0.065 moles) of 98% 1,3-propanediol di-p-tosylate. After reaction for 96 hours at 75° C., the reactor was opened, and its contents were vacuum filtered and the resulting lower fluorochemical phase separated. The fluorochemical phase was vacuum distilled and, after taking a small precut (which was discarded), was found to distill at (125-128° C.)/0.003 atmospheres, with the resulting viscous oil solidifying upon standing. By GLC, this fraction was determined to consist of four main components in a 27/62/7/4% ratio. The main two components were determined by GCMS to be isomers of the expected product shown below.

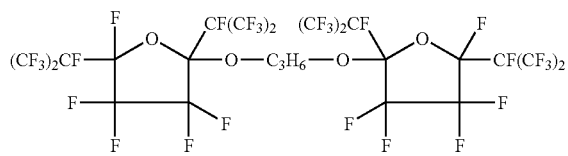

The resulting product was treated with an equal volume of 45% aqueous potassium hydroxide at reflux for 18 hours. Novec™ HFE-7100 fluid was added and the resulting lower fluorochemical phase separated, washed with water, dried over magnesium sulfate, filtered, and the solvent removed by rotary evaporation. The GLC of the resulting product showed only the first two components noted above. Its IR spectra showed no carbonyl groups.

Example 9

Reaction of $C_3F_7OCF(CF_3)COC_2F_4COCF(CF_3)OC_3F_7$ with dimethyl sulfate 8.2 grams (0.011 moles) of $C_3F_7OCF(CF_3)COC_2F_4COCF(CF_3)OC_3F_7$, 1.4 grams (0.024 moles) potassium fluoride, 3.8 grams Adogen™ 464 phase transfer catalyst (diglyme solution containing 49 weight percent catalyst), 75 grams diglyme, and 3.1 grams (0.025 moles) dimethyl sulfate were combined in a 250 mL round bottom flask equipped with a magnetic stirrer. The resulting mixture was heated to 32° C. for 18 hours. Then, a solution of 3.6 grams (0.029 moles) of aqueous potassium hydroxide (45 percent solution in water) and 100 grams water were added to the mixture, and the mixture was heated to 60° C. for one hour. The resulting product was then azeotropically distilled and washed once with water to give 6.3 grams of product. The product consisted of two main components (about 88 percent) having the same mass (m/e=760) consistent with the desired structure. A very small carbonyl absorption was also noted. However, after an additional treatment of the product with aqueous KOH, the carbonyl peak was completely gone, and the IR spectra of the product were consistent with the desired structure.

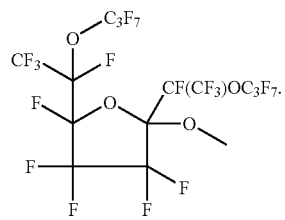

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:
1. A hydrofluoroether compound represented by one of the following general formulas (I) and (II):

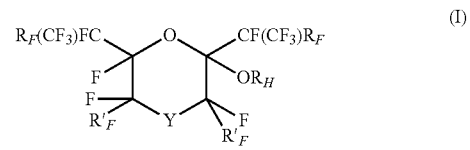

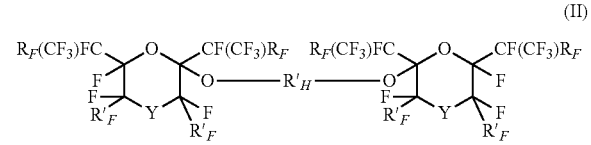

wherein each $R_F$ is independently a linear or branched perfluoroalkyl group that optionally contains at least one catenated heteroatom and that optionally comprises a terminal moiety selected from —$CF_2H$, —$CFHCF_3$, and —$CF_2OCH_3$; each $R_F'$ is independently a fluorine atom or a perfluoroalkyl group that is linear or branched and that optionally contains at least one catenated heteroatom; Y is a covalent bond, —O—, —$CF(R_F')$—, or —$N(R_F'')$—, wherein $R_F''$ is a perfluoroalkyl group that is linear or branched and that optionally contains at least one catenated heteroatom; $R_H$ is an alkyl or fluoroalkyl group that is linear, branched, cyclic, or a combination thereof and that optionally contains at least one catenated heteroatom; and $R_H'$ is an alkylene or fluoroalkylene group that is linear, branched, cyclic, or a combination thereof, that has at least two carbon atoms, and that optionally contains at least one catenated heteroatom; and wherein the catenated heteroatom is selected from divalent ether oxygen atoms or trivalent nitrogen atoms.

2. The hydrofluoroether compound of claim 1, wherein each said $R_F$ is a linear or branched perfluoroalkyl group that has from one to six carbon atoms and that optionally contains at least one catenated heteroatom; each said $R_F'$ is independently a fluorine atom or a perfluoroalkyl group having from one to four carbon atoms; said $R_H$ is a linear or branched alkyl or fluoroalkyl group having from one to eight carbon atoms; and said $R_H'$ is a linear or branched alkylene or fluoroalkylene group having from two to eight carbon atoms and at least four hydrogen atoms.

3. The hydrofluoroether compound of claim 1, wherein each said $R_F$ is a linear or branched perfluoroalkyl group that has from one to three carbon atoms and that optionally contains at least one catenated divalent ether oxygen atom; each said $R_F'$ is independently a fluorine atom or a perfluoromethyl group; said Y is a covalent bond or a perfluoromethylene group; said $R_H$ is an alkyl group having from one to four carbon atoms; and said $R_H'$ is an alkylene group having from two to four carbon atoms.

4. The hydrofluoroether compound of claim 1, wherein each said $R_F$ is a perfluoromethyl group; each said $R_F'$ is a fluorine atom; said Y is a covalent bond; said $R_H$ is an ethyl group; and said $R_H'$ is a propylene group.

5. The hydrofluoroether compound of claim 1, wherein said compound is one of said class that is represented by said general formula (I).

6. The hydrofluoroether compound of claim 1, wherein said compound is selected from

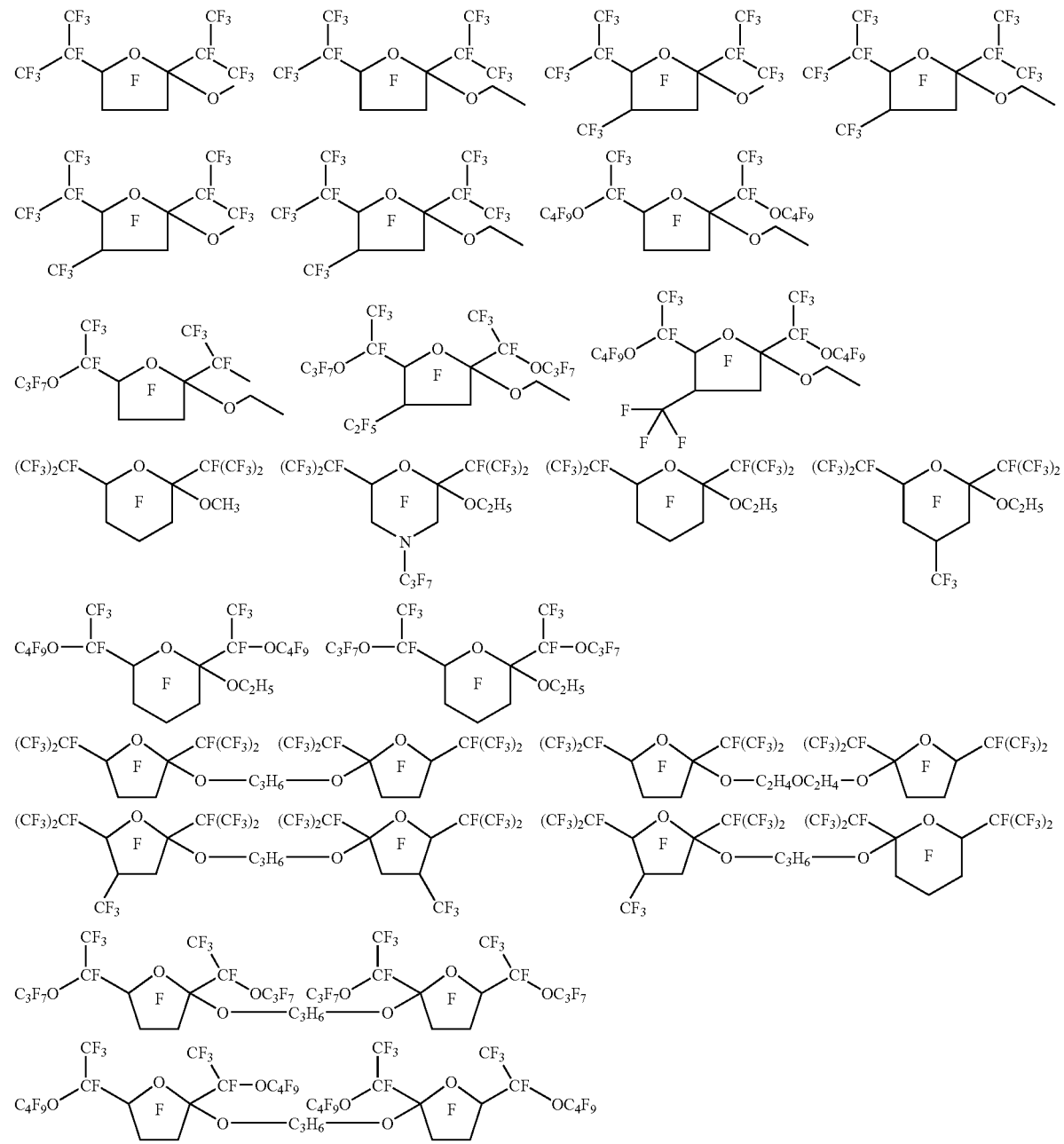

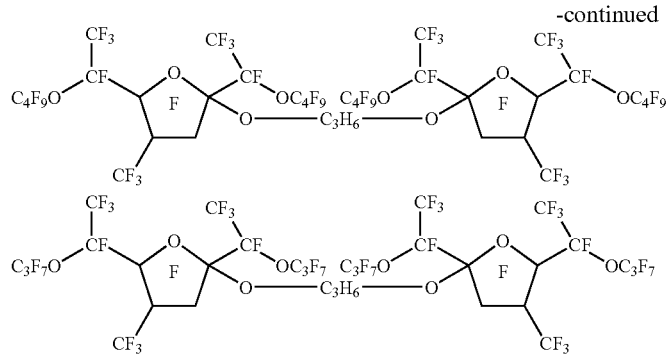

and mixtures thereof.

7. The hydrofluoroether compound of claim 1, wherein each said Y is a covalent bond; each said $R_F$ is independently a perfluoroalkyl group that optionally contains at least one catenated divalent ether oxygen atom; said $R_H$ is alkyl; and said $R_H'$ is alkylene.

8. A process for preparing the hydrofluoroether compound of claim 1 comprising (a) reacting at least one fluorochemical ketone compound with at least one fluoride source to form at least one fluorochemical alkoxide, said fluorochemical ketone compound comprising (1) two terminal, branched fluoroalkylcarbonyl or perfluoroalkylcarbonyl groups that optionally comprise at least one catenated heteroatom selected from divalent ether oxygen atoms and trivalent nitrogen atoms and (2) an intervening linear or branched perfluoroalkylene segment, said perfluoroalkylene segment optionally containing one or more catenated heteroatoms selected from divalent ether oxygen atoms and trivalent nitrogen atoms, wherein the branching of said terminal fluoroalkylcarbonyl or perfluoroalkylcarbonyl groups is at the carbon atom of said group's fluoroalkyl or perfluoroalkyl moiety that is adjacent to said group's carbonyl moiety; and (b) reacting said fluorochemical alkoxide with at least one alkylating agent to form at least one hydrofluoroether compound.

9. A process for removing a contaminant from an article comprising contacting said article with a composition comprising at least one hydrofluoroether compound of claim 1.

10. A process for preparing a foamed plastic comprising vaporizing a blowing agent mixture in the presence of at least one foamable polymer or the precursors of at least one foamable polymer, said blowing agent mixture comprising at least one hydrofluoroether compound of claim 1.

11. A process for vapor phase soldering comprising melting solder by immersing at least one component that comprises said solder in a body of fluorochemical liquid vapor that comprises at least one hydrofluoroether compound of claim 1.

12. A process for transferring heat comprising transferring heat between a heat source and a heat sink through the use of a heat transfer agent comprising at least one hydrofluoroether compound of claim 1.

13. A process for depositing a coating on a substrate comprising applying to at least a portion of at least one surface of said substrate a composition comprising (a) a solvent composition comprising at least one hydrofluoroether compound of claim 1; and (b) at least one coating material that is soluble or dispersible in said solvent composition.

14. A process for cutting or abrasive working comprising applying a working fluid to a metal, cermet, or composite workpiece and tool, said working fluid comprising at least one hydrofluoroether compound of claim 1 and at least one lubricious additive.

15. A polymerization process comprising polymerizing at least one monomer in the presence of at least one polymerization initiator and at least one hydrofluoroether compound of claim 1.

* * * * *